(12) United States Patent
Lebofsky et al.

(10) Patent No.: US 12,319,910 B2
(45) Date of Patent: *Jun. 3, 2025

(54) SECOND STRAND DIRECT

(71) Applicant: Bio-Rad Laboratories, Inc., Hercules, CA (US)

(72) Inventors: Ronald Lebofsky, Kensington, CA (US); Jeremy Agresti, Richmond, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 72 days.

This patent is subject to a terminal disclaimer.

(21) Appl. No.: 18/214,941

(22) Filed: Jun. 27, 2023

(65) Prior Publication Data

US 2024/0076658 A1 Mar. 7, 2024

Related U.S. Application Data

(63) Continuation of application No. 17/102,111, filed on Nov. 23, 2020, now Pat. No. 11,725,206, which is a continuation of application No. 16/687,411, filed on Nov. 18, 2019, now Pat. No. 10,876,112, which is a continuation of application No. 15/668,321, filed on Aug. 3, 2017, now Pat. No. 10,676,736.

(60) Provisional application No. 62/522,232, filed on Jun. 20, 2017, provisional application No. 62/371,638, filed on Aug. 5, 2016.

(51) Int. Cl.
*C12N 15/10* (2006.01)

(52) U.S. Cl.
CPC ..... *C12N 15/1096* (2013.01); *C12N 15/1065* (2013.01)

(58) Field of Classification Search
CPC ............ C12N 15/1096; C12N 15/1065; C12Q 1/6844; C12Q 2525/191; C12Q 2563/159; C12Q 2521/107; C12Q 2521/327; C12Q 2521/507; C12Q 2563/179; C12Q 2565/514
See application file for complete search history.

(56) References Cited

U.S. PATENT DOCUMENTS

| | | | |
|---|---|---|---|
| 9,074,204 | B2 | 7/2015 | Anderson et al. |
| 10,081,807 | B2 | 9/2018 | Jacobson |
| 2006/0281092 | A1 | 12/2006 | Willie et al. |
| 2010/0120098 | A1 | 5/2010 | Grunenwald et al. |
| 2012/0237943 | A1 | 9/2012 | Soldatov et al. |
| 2013/0005585 | A1* | 1/2013 | Anderson .............. C12N 15/66 435/6.12 |
| 2015/0291942 | A1 | 10/2015 | Gloeckner et al. |
| 2015/0329891 | A1 | 11/2015 | Tan et al. |
| 2016/0053253 | A1 | 2/2016 | Salathia et al. |

FOREIGN PATENT DOCUMENTS

| | | |
|---|---|---|
| WO | 2008/074891 A2 | 6/2008 |
| WO | 2010/053587 A2 | 5/2010 |
| WO | 2012/040387 A1 | 3/2012 |
| WO | 2012/162267 A2 | 11/2012 |
| WO | 2013/131962 A1 | 9/2013 |
| WO | 2013/163263 A2 | 10/2013 |
| WO | 2014/071946 A1 | 5/2014 |
| WO | 2014/201273 A1 | 12/2014 |
| WO | 2015/029031 A1 | 3/2015 |

OTHER PUBLICATIONS

The International Search Report and Written Opinion from Application No. PCT/US17/45324, dated Nov. 9, 2017.
Extended European Search Report in EP Application 17837697.6 mailed Feb. 5, 2020; 9 pages.
Caruccio, N. et al.; "Nextera™ Technology for NGS DNA Library Preparation: Simultaneous Fragmentation and Tagging by In Vitro Transposition"; Epibio; vol. 16-3; retrieved from the internet Sep. 19, 2016 at http://www.epibio.com/docs/default-source/forum-archive/forum-16-3---nextera-technology-for-ngs-dna-library-preparation---simultaneous-fragmentation-and-tagging-by-in-vitro-transposition.pdf? sfvrsn=4; Oct. 1, 2009; 3 pages.
Gertz, J. et al.; "Transposase mediated construction of RNA-seq libraries"; Genome Research; vol. 22, No. 1; Jan. 1, 2012; pp. 134-141.
Islam, S. et al.; "Characterization of the single-cell transcriptional landscape by highly multiplex RNA-seq"; Genome Research; vol. 21, No. 7; Cold Spring Harbor Press; Jul. 1, 2011; pp. 1160-1167.

* cited by examiner

*Primary Examiner* — Sahana S Kaup
(74) *Attorney, Agent, or Firm* — Kilpatrick Townsend and Stockton LLP

(57) ABSTRACT

Methods and compositions are provided herein for preparing high-throughput cDNA sequencing libraries.

18 Claims, 21 Drawing Sheets

Specification includes a Sequence Listing.

| | homoadapter version 1 | homoadapter version 2 | homoadapter version 3 | homoadapter version 4 | homoadapter version 5 | homoadapter version 6 | homoadapter version 7 | homoadapter version 8 |
|---|---|---|---|---|---|---|---|---|
| GTCTCGTGGGCTCGG;AGATGTGTATAAGAGACAG transferred strand sequence (c, B) | x | x | | | | | | |
| TCGTCGGCAGCGTC;AGATGTGTATAAGAGACAG transferred strand sequence (b, B) | | | x | x | | | | |
| AGATGTGTATAAGAGACAG transferred strand sequence (B) | | | | | x | x | x | x |
| CAAGCAGAAGACGGCATACGAGAT[i7];GTCTCGTGGGCTCGG amp primer | x | | | | x | | | |
| AATGATACGGCGACCACCGAGATCTACAC[i5];GTCTCGTGGGCTCGG amp primer | | x | | | | x | | |
| CAAGCAGAAGACGGCATACGAGAT[i7];TCGTCGGCAGCGTC amp primer | | | x | | | | x | |
| AATGATACGGCGACCACCGAGATCTACAC[i5];TCGTCGGCAGCGTC amp primer | | | | x | | | | x |
| GTCTCGTGGGCTCGG;AGATGTGTATAAGAGACAG amp primer (same as transferred strand c, B) | | | | | x | x | | |
| TCGTCGGCAGCGTC;AGATGTGTATAAGAGACAG amp primer (same as transferred strand b,B) | | | | | | | x | x |

FIG. 1A

| | heteroadapter version 9 | heteroadapter version 10 | heteroadapter version 11 | heteroadapter version 12 | heteroadapter version 13 | heteroadapter version 14 |
|---|---|---|---|---|---|---|
| GTCTCGTGGGCTCGG;AGATGTGTATAAGAGACAG transferred strand sequence (c, B) | x | x | x | x | x | x |
| TCGTCGGCAGCGTC;AGATGTGTATAAGAGACAG transferred strand sequence (b, B) | x | x | x | x | x | x |
| CAAGCAGAAGACGGCATACGAGAT[i7];GTCTCGTGGGCTCGG amp primer | x | | | x | | |
| AATGATACGGCGACCACCGAGATCTACAC[i5];GTCTCGTGGGCTCGG amp primer | | x | | | | |
| CAAGCAGAAGACGGCATACGAGAT[i7];TCGTCGGCAGCGTC amp primer | x | | | | | |
| AATGATACGGCGACCACCGAGATCTACAC[i5];TCGTCGGCAGCGT C amp primer | | x | | | | |
| GTCTCGTGGGCTCGG;AGATGTGTATAAGAGACAG amp primer (same as transferred strand c, B) | | | x | x | | x |
| TCGTCGGCAGCGTC;AGATGTGTATAAGAGACAG amp primer (same as transferred strand b, B) | | | x | x | x | x |
| AGATGTGTATAAGAGACAG amp primer (same as transferred strand B) | | | | | | |
| CAAGCAGAAGACGGCATACGAGAT[i7];GTCTCGTGGGCTCGG;AGATGTGTATAAGAGACAG amp primer | | | | | x | |
| AATGATACGGCGACCACCGAGATCTACAC[i5];TCGTCGGCAGCGT C;AGATGTGTATAAGAGACAG amp primer | | | | | | |

FIG. 1B

| Current | | Alternative 1 | | Alternative 2 | | Alternative 3 | | Alternative 4 | | Alternative 5 |
|---|---|---|---|---|---|---|---|---|---|---|
| drops | reverse transcription | drops | reverse transcription | drops | reverse transcriptase RNAseH+ | drops | reverse transcription | drops | reverse transcriptase RNAseH+ | reverse transcriptase RNAseH+ |
| bulk | RNAseH | bulk | RNAseH | bulk | Any DNA pol that extends from an RNA primer and has 5-3' exo activity | bulk | RNAseH | bulk | Any DNA pol that extends from an RNA primer and has strand displacing activity | Any DNA pol that extends from an RNA primer and has strand displacing activity |
| | DNApoll | | Any DNA pol that extends from an RNA primer and has 5-3' exo activity | | +/- ligase | | Any DNA pol that extends from an RNA primer and has strand displacing activity | | +/- ligase | |
| | ligase | | +/- ligase | | | | +/- ligase | | | |

FIG. 2

SEQUENCE LISTING

```
Sequence total quantity: 39
SEQ ID NO: 1                moltype = DNA   length = 31
FEATURE                     Location/Qualifiers
misc_feature                1..31
                            note = synthetic nucleotide sequence
source                      1..31
                            mol_type = other DNA
                            organism = synthetic construct
SEQUENCE: 1
aatgagatac ggcgaccacc gagatctaca c                                       31

SEQ ID NO: 2                moltype = DNA   length = 24
FEATURE                     Location/Qualifiers
misc_feature                1..24
                            note = synthetic nucleotide sequence
source                      1..24
                            mol_type = other DNA
                            organism = synthetic construct
SEQUENCE: 2
caagcagaag acggcatacg agat                                               24

SEQ ID NO: 3                moltype = DNA   length = 51
FEATURE                     Location/Qualifiers
misc_feature                1..51
                            note = synthetic nucleotide sequence
misc_difference             25..28
                            note = misc_feature - n is a, c, g, or t
misc_difference             29..36
                            note = misc_feature - n is a, c, g, or t; n may be present
                             or absent
source                      1..51
                            mol_type = other DNA
                            organism = synthetic construct
SEQUENCE: 3
caagcagaag acggcatacg agatnnnnnn nnnnnngtct cgtgggctcg g                  51

SEQ ID NO: 4                moltype = DNA   length = 50
FEATURE                     Location/Qualifiers
misc_feature                1..50
                            note = synthetic nucleotide sequence
misc_difference             25..28
                            note = misc_feature - n is a, c, g, or t
misc_difference             29..36
                            note = misc_feature - n is a, c, g, or t; n may be present
                             or absent
source                      1..50
                            mol_type = other DNA
                            organism = synthetic construct
SEQUENCE: 4
caagcagaag acggcatacg agatnnnnnn nnnnnntcgt cggcagcgtc                   50

SEQ ID NO: 5                moltype = DNA   length = 58
FEATURE                     Location/Qualifiers
misc_feature                1..58
                            note = synthetic nucleotide sequence
misc_difference             32..35
                            note = misc_feature - n is a, c, g, or t
misc_difference             36..43
                            note = misc_feature - n is a, c, g, or t; n may be present
                             or absent
source                      1..58
                            mol_type = other DNA
                            organism = synthetic construct
SEQUENCE: 5
aatgagatac ggcgaccacc gagatctaca cnnnnnnnnn nnngtctcgt gggctcgg          58

SEQ ID NO: 6                moltype = DNA   length = 57
FEATURE                     Location/Qualifiers
misc_feature                1..57
                            note = synthetic nucleotide sequence
misc_difference             32..35
                            note = misc_feature - n is a, c, g, or t
misc_difference             36..43
                            note = misc_feature - n is a, c, g, or t; n may be present
                             or absent
source                      1..57
                            mol_type = other DNA
                            organism = synthetic construct
```

-continued

```
SEQUENCE: 6
aatgagatac ggcgaccacc gagatctaca cnnnnnnnnn nnntcgtcgg cagcgtc        57

SEQ ID NO: 7                moltype = DNA   length = 15
FEATURE                     Location/Qualifiers
misc_feature                1..15
                            note = synthetic nucleotide sequence
source                      1..15
                            mol_type = other DNA
                            organism = synthetic construct
SEQUENCE: 7
gtctcgtggg ctcgg                                                      15

SEQ ID NO: 8                moltype = DNA   length = 14
FEATURE                     Location/Qualifiers
misc_feature                1..14
                            note = synthetic nucleotide sequence
source                      1..14
                            mol_type = other DNA
                            organism = synthetic construct
SEQUENCE: 8
tcgtcggcag cgtc                                                       14

SEQ ID NO: 9                moltype = DNA   length = 37
FEATURE                     Location/Qualifiers
misc_feature                1..37
                            note = synthetic nucleotide sequence
source                      1..37
                            mol_type = other DNA
                            organism = synthetic construct
SEQUENCE: 9
gcctgtccgc ggaagcagtg gtatcaacgc agagtac                              37

SEQ ID NO: 10               moltype = DNA   length = 19
FEATURE                     Location/Qualifiers
misc_feature                1..19
                            note = synthetic nucleotide sequence
source                      1..19
                            mol_type = other DNA
                            organism = synthetic construct
SEQUENCE: 10
agatgtgtat aagagacag                                                  19

SEQ ID NO: 11               moltype = DNA   length = 19
FEATURE                     Location/Qualifiers
misc_feature                1..19
                            note = synthetic nucleotide sequence
source                      1..19
                            mol_type = other DNA
                            organism = synthetic construct
SEQUENCE: 11
agatgtgtat aagagacag                                                  19

SEQ ID NO: 12               moltype = DNA   length = 34
FEATURE                     Location/Qualifiers
misc_feature                1..34
                            note = synthetic nucleotide sequence
source                      1..34
                            mol_type = other DNA
                            organism = synthetic construct
SEQUENCE: 12
gtctcgtggg ctcggagatg tgtataagag acag                                 34

SEQ ID NO: 13               moltype = DNA   length = 19
FEATURE                     Location/Qualifiers
misc_feature                1..19
                            note = synthetic nucleotide sequence
source                      1..19
                            mol_type = other DNA
                            organism = synthetic construct
SEQUENCE: 13
ctgtctctta tacacatct                                                  19

SEQ ID NO: 14               moltype = DNA   length = 33
FEATURE                     Location/Qualifiers
misc_feature                1..33
                            note = synthetic nucleotide sequence
source                      1..33
                            mol_type = other DNA
```

```
                      organism = synthetic construct
SEQUENCE: 14
acactctttc cctacacgac gctcttccga tct                                33

SEQ ID NO: 15         moltype = DNA  length = 29
FEATURE               Location/Qualifiers
misc_feature          1..29
                      note = synthetic nucleotide sequence
source                1..29
                      mol_type = other DNA
                      organism = synthetic construct
SEQUENCE: 15
aatgatacgg cgaccaccga gatctacac                                     29

SEQ ID NO: 16         moltype = DNA  length = 56
FEATURE               Location/Qualifiers
misc_feature          1..56
                      note = synthetic nucleotide sequence
misc_difference       30..33
                      note = misc_feature - n is a, c, g, or t
misc_difference       34..41
                      note = misc_feature - n is a, c, g, or t; n may be present
                       or absent
source                1..56
                      mol_type = other DNA
                      organism = synthetic construct
SEQUENCE: 16
aatgatacgg cgaccaccga gatctacacn nnnnnnnnnn ngtctcgtgg gctcgg       56

SEQ ID NO: 17         moltype = DNA  length = 55
FEATURE               Location/Qualifiers
misc_feature          1..55
                      note = synthetic nucleotide sequence
misc_difference       30..33
                      note = misc_feature - n is a, c, g, or t
misc_difference       34..41
                      note = misc_feature - n is a, c, g, or t; n may be present
                       or absent
source                1..55
                      mol_type = other DNA
                      organism = synthetic construct
SEQUENCE: 17
aatgatacgg cgaccaccga gatctacacn nnnnnnnnnn ntcgtcggca gcgtc        55

SEQ ID NO: 18         moltype = DNA  length = 33
FEATURE               Location/Qualifiers
misc_feature          1..33
                      note = synthetic nucleotide sequence
source                1..33
                      mol_type = other DNA
                      organism = synthetic construct
SEQUENCE: 18
tcgtcggcag cgtcagatgt gtataagaga cag                                33

SEQ ID NO: 19         moltype = DNA  length = 70
FEATURE               Location/Qualifiers
misc_feature          1..70
                      note = synthetic nucleotide sequence
misc_difference       25..28
                      note = misc_feature - n is a, c, g, or t
misc_difference       29..36
                      note = misc_feature - n is a, c, g, or t; n may be present
                       or absent
source                1..70
                      mol_type = other DNA
                      organism = synthetic construct
SEQUENCE: 19
caagcagaag acggcatacg agatnnnnnnnn nnnnnngtct cgtgggctcg gagatgtgta 60
taagagacag                                                          70

SEQ ID NO: 20         moltype = DNA  length = 74
FEATURE               Location/Qualifiers
misc_feature          1..74
                      note = synthetic nucleotide sequence
misc_difference       30..33
                      note = misc_feature - n is a, c, g, or t
misc_difference       34..41
                      note = misc_feature - n is a, c, g, or t; n may be present
                       or absent
```

```
source                        1..74
                              mol_type = other DNA
                              organism = synthetic construct
SEQUENCE: 20
aatgatacgg cgaccaccga gatctacacn nnnnnnnnn ntcgtcggca gcgtcagatg      60
tgtataagag acag                                                       74

SEQ ID NO: 21                 moltype = DNA  length = 48
FEATURE                       Location/Qualifiers
misc_feature                  1..48
                              note = synthetic nucleotide sequence
source                        1..48
                              mol_type = other DNA
                              organism = synthetic construct
SEQUENCE: 21
tcgtcggcag cgtcagatgt gtataagaga gatgtgtata agagacag                  48

SEQ ID NO: 22                 moltype = DNA  length = 29
FEATURE                       Location/Qualifiers
misc_feature                  1..29
                              note = synthetic nucleotide sequence
source                        1..29
                              mol_type = other DNA
                              organism = synthetic construct
SEQUENCE: 22
tcgtcggcag cgtcagatgt gtataagag                                       29

SEQ ID NO: 23                 moltype = DNA  length = 57
FEATURE                       Location/Qualifiers
misc_feature                  1..57
                              note = synthetic nucleotide sequence
source                        1..57
                              mol_type = other DNA
                              organism = synthetic construct
SEQUENCE: 23
aatgatacgg cgaccaccga gatctacatc gtcggcacgc tcagatgtgt ataagag        57

SEQ ID NO: 24                 moltype = DNA  length = 73
FEATURE                       Location/Qualifiers
misc_feature                  1..73
                              note = synthetic nucleotide sequence
misc_difference               34..37
                              note = misc_feature - n is a, c, g, or t
misc_difference               38..45
                              note = misc_feature - n is a, c, g, or t; n may be present
                               or absent
source                        1..73
                              mol_type = other DNA
                              organism = synthetic construct
SEQUENCE: 24
ctgtctctta tacacatctg acgctgccga cgannnnnnn nnnnngtgta gtctcggtgg     60
tcgccgtatc att                                                        73

SEQ ID NO: 25                 moltype = DNA  length = 70
FEATURE                       Location/Qualifiers
misc_feature                  1..70
                              note = synthetic nucleotide sequence
misc_difference               25..28
                              note = misc_feature - n is a, c, g, or t
misc_difference               29..36
                              note = misc_feature - n is a, c, g, or t; n may be present
                               or absent
source                        1..70
                              mol_type = other DNA
                              organism = synthetic construct
SEQUENCE: 25
caagcagaag acggcatacg agatnnnnnn nnnnnngtct cgtgggctcg gagatgtgta     60
taagagagag                                                            70

SEQ ID NO: 26                 moltype = DNA  length = 69
FEATURE                       Location/Qualifiers
misc_feature                  1..69
                              note = synthetic nucleotide sequence
misc_difference               35..38
                              note = misc_feature - n is a, c, g, or t
misc_difference               39..46
                              note = misc_feature - n is a, c, g, or t; n may be present
                               or absent
source                        1..69
```

```
                        mol_type = other DNA
                        organism = synthetic construct
SEQUENCE: 26
ctgtctctta tacacatctc cgagcccacg agacnnnnnn nnnnnnatct cgtatgccgc    60
ttctgcttg                                                           69

SEQ ID NO: 27           moltype = DNA   length = 49
FEATURE                 Location/Qualifiers
misc_feature            1..49
                        note = synthetic nucleotide sequence
misc_difference         24..27
                        note = misc_feature - n is a, c, g, or t
misc_difference         28..35
                        note = misc_feature - n is a, c, g, or t; n may be present
                         or absent
source                  1..49
                        mol_type = other DNA
                        organism = synthetic construct
SEQUENCE: 27
caagcagaag acggatacga gatnnnnnnn nnnnntcgtc ggcagcgtc                49

SEQ ID NO: 28           moltype = DNA   length = 68
FEATURE                 Location/Qualifiers
misc_feature            1..68
                        note = synthetic nucleotide sequence
misc_difference         25..28
                        note = misc_feature - n is a, c, g, or t
misc_difference         29..36
                        note = misc_feature - n is a, c, g, or t; n may be present
                         or absent
source                  1..68
                        mol_type = other DNA
                        organism = synthetic construct
SEQUENCE: 28
caagcagaag acggcatacg agatnnnnnn nnnnnntcgt cggcagcgtc agatgtgtat    60
aagaacag                                                            68

SEQ ID NO: 29           moltype = DNA   length = 68
FEATURE                 Location/Qualifiers
misc_feature            1..68
                        note = synthetic nucleotide sequence
misc_difference         34..37
                        note = misc_feature - n is a, c, g, or t
misc_difference         38..45
                        note = misc_feature - n is a, c, g, or t; n may be present
                         or absent
source                  1..68
                        mol_type = other DNA
                        organism = synthetic construct
SEQUENCE: 29
ctgtctctta tacacatctg acgctgccga cgannnnnnn nnnnnatctc gtatgccgct    60
tctgcttg                                                            68

SEQ ID NO: 30           moltype = DNA   length = 56
FEATURE                 Location/Qualifiers
misc_feature            1..56
                        note = synthetic nucleotide sequence
misc_difference         25..28
                        note = misc_feature - n is a, c, g, or t
misc_difference         29..36
                        note = misc_feature - n is a, c, g, or t; n may be present
                         or absent
source                  1..56
                        mol_type = other DNA
                        organism = synthetic construct
SEQUENCE: 30
caagcagaag acggcatacg agatnnnnnn nnnnnngtct cgtgggctcg gctcgg        56

SEQ ID NO: 31           moltype = DNA   length = 69
FEATURE                 Location/Qualifiers
misc_feature            1..69
                        note = synthetic nucleotide sequence
misc_difference         25..28
                        note = misc_feature - n is a, c, g, or t
misc_difference         29..36
                        note = misc_feature - n is a, c, g, or t; n may be present
                         or absent
source                  1..69
                        mol_type = other DNA
```

```
                              organism = synthetic construct
SEQUENCE: 31
caagcagaag acggcatacg agatnnnnnn nnnnnngtct cgtgggctcg gagatgtgta    60
taagagcag                                                           69

SEQ ID NO: 32          moltype = DNA   length = 66
FEATURE                Location/Qualifiers
misc_feature           1..66
                       note = synthetic nucleotide sequence
source                 1..66
                       mol_type = other DNA
                       organism = synthetic construct
SEQUENCE: 32
aatgatacgg cgaccaccga gatctacacg cctgtccgcg gaagcagtgg tatcaacgca    60
gagtac                                                              66

SEQ ID NO: 33          moltype = DNA   length = 69
FEATURE                Location/Qualifiers
misc_feature           1..69
                       note = synthetic nucleotide sequence
misc_difference        25..28
                       note = misc_feature - n is a, c, g, or t
misc_difference        29..36
                       note = misc_feature - n is a, c, g, or t; n may be present
                        or absent
source                 1..69
                       mol_type = other DNA
                       organism = synthetic construct
SEQUENCE: 33
caagcagaag acggcatacg agatnnnnnn nnnnnntcgt cggcagcgtc agatgtgtat    60
aagagacag                                                           69

SEQ ID NO: 34          moltype = DNA   length = 69
FEATURE                Location/Qualifiers
misc_feature           1..69
                       note = synthetic nucleotide sequence
misc_difference        34..37
                       note = misc_feature - n is a, c, g, or t
misc_difference        38..45
                       note = misc_feature - n is a, c, g, or t; n may be present
                        or absent
source                 1..69
                       mol_type = other DNA
                       organism = synthetic construct
SEQUENCE: 34
ctgtctctta tacacatctg acgctgccga cgannnnnnn nnnnnatctc gtatgccgtc    60
ttctgcttg                                                           69

SEQ ID NO: 35          moltype = DNA   length = 70
FEATURE                Location/Qualifiers
misc_feature           1..70
                       note = synthetic nucleotide sequence
misc_difference        35..38
                       note = misc_feature - n is a, c, g, or t
misc_difference        39..46
                       note = misc_feature - n is a, c, g, or t; n may be present
                        or absent
source                 1..70
                       mol_type = other DNA
                       organism = synthetic construct
SEQUENCE: 35
ctgtctctta tacacatctc cgagcccacg agacnnnnnn nnnnnnatct cgtatgccgt    60
cttctgcttg                                                          70

SEQ ID NO: 36          moltype = DNA   length = 66
FEATURE                Location/Qualifiers
misc_feature           1..66
                       note = synthetic nucleotide sequence
source                 1..66
                       mol_type = other DNA
                       organism = synthetic construct
SEQUENCE: 36
gtactctgcg ttgataccac tgcttccgcg gacaggcgtg tagatctcgg tggtcgccgt    60
atcatt                                                              66

SEQ ID NO: 37          moltype = DNA   length = 34
FEATURE                Location/Qualifiers
misc_feature           1..34
                       note = synthetic nucleotide sequence
```

```
source              1..34
                    mol_type = other DNA
                    organism = synthetic construct
SEQUENCE: 37
ctgtctctta tacacatctc cgagcccacg agac                            34

SEQ ID NO: 38       moltype = DNA  length = 33
FEATURE             Location/Qualifiers
misc_feature        1..33
                    note = synthetic nucleotide sequence
source              1..33
                    mol_type = other DNA
                    organism = synthetic construct
SEQUENCE: 38
ctgtctctta tacacatctg acgctgccga cga                             33

SEQ ID NO: 39       moltype = DNA  length = 30
FEATURE             Location/Qualifiers
misc_feature        1..30
                    note = synthetic nucleotide sequence
source              1..30
                    mol_type = other DNA
                    organism = synthetic construct
SEQUENCE: 39
gtctcgtggg ctcggagatg tgtataagag                                 30
```

Second strand direct to Tagmentase sample prep results reproducibility

| USER | 1 | 1 | 2 | 3 |
|---|---|---|---|---|
| Replicate | 1 | 2 | 1 | 1 |
| Hydrogel particle lot | 1 | 1 | 2 | 2 |
| Number of Cells (single) | Measured | Measured | Measured | Measured |
| | 436 | 433 | 329 | 578 |
| Crosstalk | 0.08 | 0.1 | 0.1 | 0.9 |
| Purity | 0.99 | 0.99 | 0.99 | 0.99 |
| Sensitivity (median genes per cell) | 4546 human, 3845 mouse | 4643 human, 4143 mouse | 4115 human, 3363 mouse | 4799 human, 4063 mouse |
| Purity | 0.99 | 0.99 | 0.99 | 0.99 |

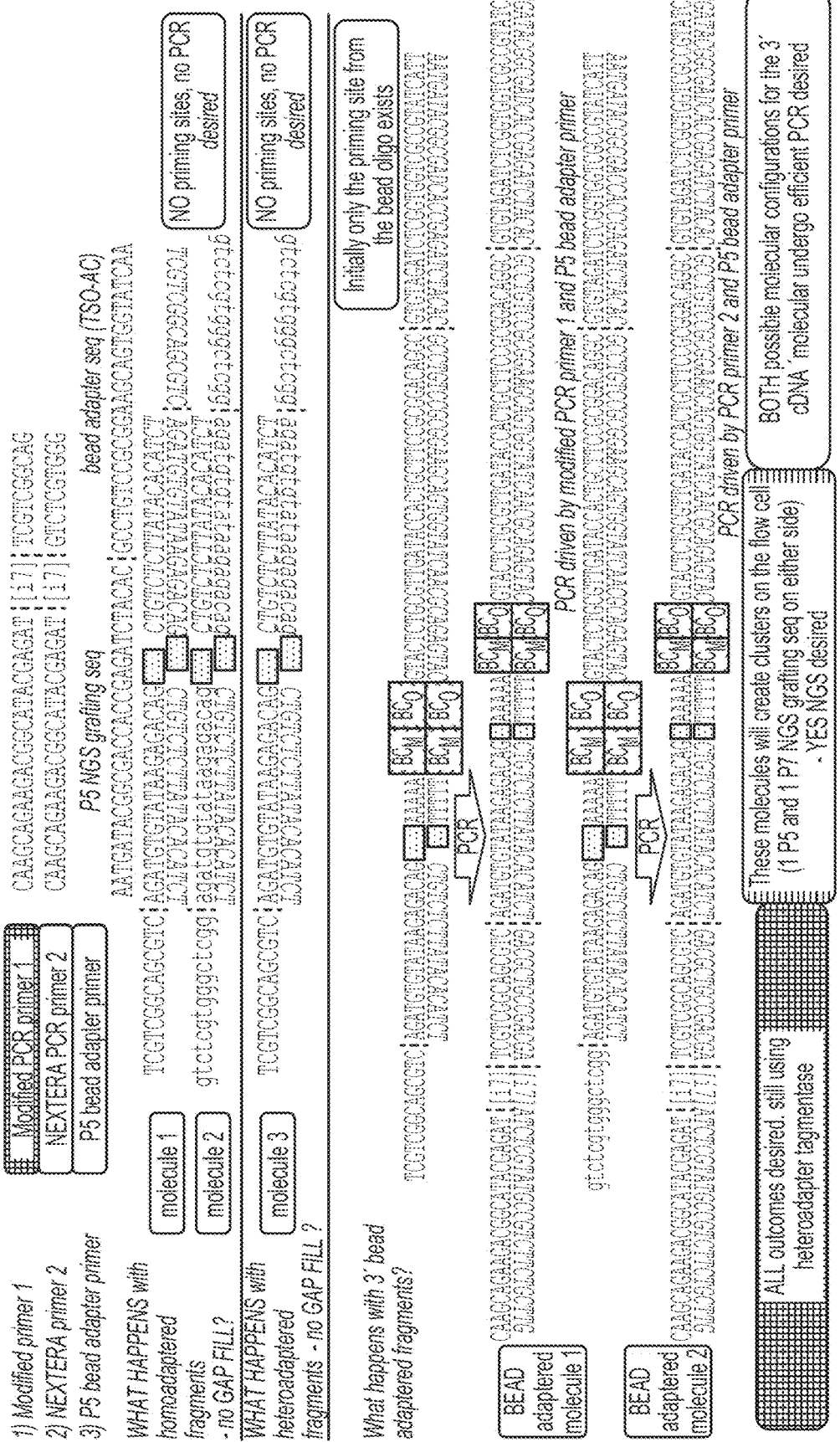

Result: increasing 2nd strand direct yield by a factor of 2, without making homoadapted tagmentase

SECOND STRAND DIRECT

CROSS-REFERENCES TO RELATED APPLICATIONS

This application is a continuation of U.S. patent application Ser. No. 17/102,111, filed Nov. 23, 2020, which is a continuation of U.S. patent application Ser. No. 16/687,411, filed Nov. 18, 2019, which is a continuation of U.S. patent application Ser. No. 15/668,321, filed Aug. 3, 2017, which claims priority to U.S. Provisional Application No. 62/371,638, filed on Aug. 5, 2016 and U.S. Provisional Application No. 62/522,232, filed on Jun. 20, 2017, all of which are hereby incorporated by reference in their entireties for all purposes.

REFERENCE TO SUBMISSION OF A SEQUENCE LISTING

The Sequence Listing written in file 094868-1392658_112250US_SL.xml created on Jul. 19, 2023, 67,590 bytes in size, is hereby incorporated by reference in its entirety for all purposes.

BACKGROUND OF THE INVENTION

High-throughput sequencing is revolutionizing many fields of biology, including cancer diagnostics, disease monitoring, and environmental analysis. In particular, methods of analyzing mRNA molecules by high-throughput sequencing of reverse transcribed cDNAs can reveal the identify and quantity of transcripts in a biological sample at a given moment in time. Thus, splicing, post-transcriptional modification, gene fusions, mutations, and changes in gene expression can all be monitored by a single method.

The input material for commonly used high-throughput sequencing platforms, such as platforms provided by Illumina, Roche Sequencing, Pacific Biosciences, and others, consists of complex libraries of transcriptome-derived DNA fragments flanked by platform-specific adaptors. The standard method for constructing such libraries is entirely in vitro and typically includes one or more, or all, of cDNA synthesis, fragmentation of DNA (mechanical or enzymatic), end-polishing, ligation of adaptor sequences, gel-based size-selection, and PCR amplification. This core protocol may be preceded by additional steps depending on the specific application. However, current methods for generating a cDNA that is tagged on both ends with adapters that are compatible with currently available high-throughput sequencing platforms generally suffer from low yields, lack of reproducibility, high cost, or a combination thereof.

BRIEF SUMMARY OF THE INVENTION

In one aspect, the present invention provides a method for tagging a cDNA polynucleotide, the method comprising: —providing a double-stranded mRNA:cDNA hybrid comprising a first strand cDNA polynucleotide having a 5' end and a 3' end and hybridized to a complementary mRNA having a 5' end and a 3' end, wherein the 5' end of the first strand cDNA polynucleotide comprises a first adapter sequence or complement thereof; —synthesizing one or more second strand cDNA polynucleotides that are complementary to and hybridized to the first strand cDNA polynucleotide, wherein synthesizing comprises: i) contacting the mRNA:cDNA hybrid with an enzyme comprising RNase H activity, thereby producing mRNA fragments hybridized to the first strand cDNA, and ii) contacting the mRNA fragments with a DNA polymerase, thereby extending the mRNA fragments in a template-directed polymerase reaction, wherein the template is the first strand cDNA polynucleotide and forming a double-stranded cDNA polynucleotide; —optionally contacting the one or more second strand cDNA polynucleotides with a DNA ligase; —contacting the double-stranded cDNA polynucleotide with an adapter-loaded tagmentase, thereby forming a reaction mixture comprising a tagged double-stranded cDNA polynucleotide comprising a first end and a second end, wherein the first end comprises the first adapter sequence and complement thereof, and the second end comprises a second adapter sequence and complement thereof, —wherein the 5' end of the mRNA is single stranded; or—wherein the 5' end of the mRNA comprises a DNA:RNA hybrid, and wherein the method comprises amplifying the tagged double-stranded cDNA in a reaction mixture comprising a first amplification primer that hybridizes to the first end and a second and third amplification primer, wherein the second or third amplification primer hybridizes to the second end; or—wherein the contacting the double-stranded cDNA polynucleotide with the adapter-loaded tagmentase is performed in a reaction mixture that contains a homo adapter-loaded tagmentase and does not contain adapter-loaded tagmentases having a different adapter.

In some embodiments, the 5' end of the mRNA is single-stranded. In some embodiments, the method further comprises selectively amplifying from the reaction mixture the tagged double-stranded cDNA polynucleotide by contacting the tagged double-stranded cDNA polynucleotide with a first amplification primer and a second amplification primer, wherein the first amplification primer selectively hybridizes to the first adapter sequence and comprises a first sequencing-platform-specific adapter sequence, and wherein the second amplification primer selectively hybridizes to the second adapter sequence and comprises a second sequencing-platform-specific adapter sequence, thereby producing a sequencing platform-specific cDNA amplicon.

In some embodiments, the providing the double-stranded mRNA:cDNA hybrid comprises contacting the mRNA with a reverse transcriptase and a first strand synthesis primer to thereby extend the first strand synthesis primer in an mRNA template-directed DNA polymerase reaction, wherein the first strand synthesis primer comprises a 3' poly-thymine end region and a 5' end comprising the first adapter sequence or complement thereof, thereby synthesizing the first strand cDNA polynucleotide hybridized to the complementary mRNA, and wherein the 5' end of the first strand cDNA comprises the first adapter sequence or complement thereof.

In some embodiments, the reverse transcriptase comprises RNase H activity, and contacting the mRNA:cDNA hybrid with the enzyme comprising RNase H activity comprises incubating the mRNA:cDNA hybrid in the presence of the reverse transcriptase to thereby produce the mRNA fragments hybridized to the first strand cDNA. In some embodiments, the contacting the mRNA:cDNA hybrid with the enzyme comprising RNase H activity comprises contacting the mRNA:cDNA hybrid with an enzyme that does not comprise reverse transcriptase activity or that is a structurally different reverse transcriptase from a reverse transcriptase used in an mRNA template-directed DNA polymerase reaction that thereby extends a first strand synthesis primer and synthesizes the first strand cDNA polynucleotide hybridized to the complementary mRNA, wherein the 5' end of the mRNA is single-stranded and the 5' end of the first strand cDNA comprises the first adapter sequence or complement thereof.

In some embodiments, the method comprises performing the mRNA template-directed DNA polymerase reaction in a reaction mixture comprising mRNA from a single cell, and the contacting the mRNA:cDNA hybrid with the enzyme comprising RNase H activity is performed in a reaction mixture comprising mRNA from at least 10 cells, preferably 50 to 500 cells. In some embodiments, the method comprises performing the mRNA template-directed DNA polymerase reaction in a reaction mixture comprising mRNA from at least 10 cells, preferably 50 to 500 cells. In some embodiments, the method comprises contacting the mRNA fragments with a DNA polymerase comprising 5'-3' exonuclease activity. In some embodiments, the method comprises contacting the mRNA fragments with a DNA polymerase comprising strand-displacement activity.

In some embodiments, the first strand synthesis primer comprises a molecular barcode or a partition-specific barcode, or a combination thereof. In some embodiments, the 5' end of the first strand cDNA polynucleotide comprises a molecular barcode or a partition-specific barcode, or a combination thereof. In some embodiments, the first end of the tagged double-stranded cDNA polynucleotide comprises adapter sequence A and the second end of the tagged double-stranded cDNA polynucleotide comprises adapter sequence B, and the method comprises selectively amplifying from the reaction mixture the tagged double-stranded cDNA polynucleotide, thereby producing a sequencing platform-specific cDNA amplicon, by contacting the tagged double-stranded cDNA polynucleotide with the first amplification primer, the second amplification primer, and a third amplification primer, —wherein the first amplification primer comprises a 3' region having a sequence A' that selectively hybridizes to the first adapter sequence A and the first amplification primer further comprises a 5' region comprising a first sequencing-platform-specific adapter sequence; and—wherein the second amplification primer and third amplification primer each comprise a 5' region comprising a second sequencing-platform-specific adapter sequence, and a 3' region, wherein the 3' region of the second or third amplification primer has a sequence B' that selectively hybridizes to the second adapter sequence B.

In some embodiments, the selectively amplifying from the reaction mixture is performed in reaction mixture that does not comprise an amplification primer containing SEQ ID NO:7. In some embodiments, the selectively amplifying from the reaction mixture is performed in reaction mixture that does not comprise an amplification primer containing SEQ ID NO:8. In some embodiments: —the first amplification primer comprises from 5' to 3' AATGAGATACGGCGACCACCGAGATCTACAC (SEQ ID NO:1) and the second amplification primer comprises from 5' to 3' CAAGCAGAAGACGGCATACGAGAT (SEQ ID NO:2); or—the first amplification primer comprises SEQ ID NO:2 and the second amplification primer comprises SEQ ID NO:1.

In some embodiments, —the first amplification primer comprises SEQ ID NO:1 and the second amplification primer comprises from 5' to 3' CAAGCAGAAGACGGCATACGAGAT[i7]GTCTCGTGGGCTCGG (SEQ ID NO:3), wherein [i7] is an index region that is present or absent, and comprises from 4-12 nucleotides; or—the first amplification primer comprises SEQ ID NO:1 and the second amplification primer comprises from 5' to 3' CAAGCAGAAGACGGCATACGAGAT[i7] TCGTCGGCAGCGTC (SEQ ID NO:4), wherein [i5] is an index region that is present or absent, and comprises from 4-12 nucleotides.

In some embodiments, the amplifying from the reaction mixture the tagged double-stranded cDNA polynucleotide comprises contacting the tagged double-stranded cDNA polynucleotide with the first amplification primer comprising SEQ ID NO:1 and a two different second amplification primers, wherein one second amplification primer comprises SEQ ID NO:3 and the other second amplification primer comprises SEQ ID NO:4. In some embodiments, —the first amplification primer comprises SEQ ID NO:2 and the second amplification primer comprises from 5' to 3' AATGAGATACGGCGACCACCGAGATCTACAC [i5] GTCTCGTGGGCTCGG (SEQ ID NO:5), wherein [i5] is an index region that is present or absent, and comprises from 4-12 nucleotides; or—the first amplification primer comprises SEQ ID NO:2 and the second amplification primer comprises from 5' to 3' AATGAGATACGGCGACCACCGAGATCTACAC [i5]TCGTCGGCAGCGTC (SEQ ID NO:6), wherein [i7] is an index region that is present or absent, and comprises from 4-12 nucleotides.

In some embodiments, the amplifying from the reaction mixture the tagged double-stranded cDNA polynucleotide comprises contacting the tagged double-stranded cDNA polynucleotide with the first amplification primer comprising SEQ ID NO:2 and a two different second amplification primers, wherein one second amplification primer comprises SEQ ID NO:5 and the other second amplification primer comprises SEQ ID NO:6. In some embodiments, the contacting the double-stranded cDNA polynucleotide with the adapter-loaded tagmentase comprises introducing a homoadapter-loaded tagmentase comprising two identical polynucleotide adapters into the reaction mixture comprising the double-stranded cDNA polynucleotide, thereby attaching one of the polynucleotide adapters to the second end of the double-stranded cDNA.

In some embodiments, the attaching is performed in a reaction mixture that does not comprise an adapter-loaded tagmentase comprising a polynucleotide adapter that is different from the two identical polynucleotide adapters of the homoadapter-loaded tagmentase. In some embodiments, the contacting the double-stranded cDNA polynucleotide with the adapter-loaded tagmentase comprises: —introducing a heteroadapter-loaded tagmentase comprising two structurally distinct polynucleotide adapters into the reaction mixture comprising the double-stranded cDNA polynucleotide; or—introducing into the reaction mixture comprising the double-stranded cDNA polynucleotide a first and a second homoadapter-loaded tagmentase wherein the first homoadapter-loaded tagmentase comprises a polynucleotide adapter and the second homoadapter tagmentase comprises a structurally distinct polynucleotide adapter, thereby attaching one of the polynucleotide adapters to the second end of the double-stranded cDNA.

In some embodiments, the homoadapter loaded tagmentase comprises a polynucleotide adapter with a single-stranded region comprising from 5' to 3' GTCTCGTGGGCTCGG (SEQ ID NO:7) or a polynucleotide adapter with a single-stranded region comprising from 5' to 3' TCGTCGGCAGCGTC (SEQ ID NO:8). In some embodiments, the homoadapter loaded tagmentase comprises the polynucleotide adapter with the single-stranded region comprising SEQ ID NO:7, the first amplification primer comprises SEQ ID NO:1, SEQ ID NO:8, or a complement thereof, and the second amplification primer comprises SEQ ID NO:7 or a complement thereof. In some embodiments, the homoadapter loaded tagmentase comprises the polynucleotide adapter with the single-stranded region comprising SEQ ID NO:7, the first amplification primer comprises SEQ ID NO:1 or a complement thereof, and the second amplification primer comprises SEQ ID NO:2, 3, or 4, or a complement thereof.

In some embodiments, the homoadapter loaded tagmentase comprises the polynucleotide adapter with the single-stranded region comprising SEQ ID NO:7, the first amplification primer comprises SEQ ID NO:2 or a complement thereof, and the second amplification primer comprises SEQ ID NO:1, 5, or 6, or a complement thereof. In some embodiments, the homoadapter loaded tagmentase comprises the polynucleotide adapter with the single-stranded region comprising SEQ ID NO:8, the first amplification primer comprises SEQ ID NO:7 or a complement thereof, and the second amplification primer comprises SEQ ID NO:8 or a complement thereof.

In some embodiments, the heteroadapter loaded tagmentase comprises a first polynucleotide adapter comprising SEQ ID NO:7 and a second polynucleotide adapter comprising SEQ ID NO:8. In some embodiments, the first amplification primer comprises SEQ ID NO:1 or the complement thereof and the second amplification primer comprises SEQ ID NO:4 or the complement thereof, and the method further comprises contacting the tagged double-stranded cDNA polynucleotide with a third amplification primer comprising SEQ ID NO:3 or a complement thereof. In some embodiments, the first amplification primer comprises SEQ ID NO:2 or the complement thereof and the second amplification primer comprises SEQ ID NO:5 or the complement thereof, and the method further comprises contacting the tagged double-stranded cDNA polynucleotide with a third amplification primer comprising SEQ ID NO:6 or a complement thereof. In some embodiments, the double-stranded cDNA polynucleotide contacted with the adapter-loaded tagmentase comprises an original first strand cDNA polynucleotide hybridized to an original second strand cDNA polynucleotide.

In another aspect, the present invention provides, a method for tagging a plurality of cDNA polynucleotides, the method comprising performing a method according to any one of the foregoing aspects or embodiments, with a plurality of structurally distinct mRNA:cDNA hybrids. In some embodiments, the plurality of structurally distinct mRNA:cDNA hybrids comprise mRNA from a single cell. In some embodiments, the plurality of structurally distinct mRNA:cDNA hybrids comprise mRNA from at least 10 cells, preferably from 50 to 500 cells. In some embodiments, the method comprises combining a plurality of reaction mixtures containing mRNA:cDNA hybrids, wherein the individual reaction mixtures comprise mRNA:cDNA hybrids from a single cell, and then synthesizing the second strand cDNA polynucleotides from the combined mRNA:cDNA hybrids. In some embodiments, the method comprises combining a plurality of reaction mixtures containing mRNA:cDNA hybrids, wherein the individual reaction mixtures comprise mRNA:cDNA hybrids from a single cell, and then contacting the combined mRNA:cDNA hybrids with an enzyme comprising RNase H activity.

In some embodiments, the method comprises combining a plurality of reaction mixtures containing mRNA:cDNA hybrids, wherein the individual reaction mixtures comprise mRNA:cDNA hybrids from a single cell and wherein the mRNA is RNase H fragmented, and then contacting the combined RNase H-fragmented mRNA:cDNA hybrids with a DNA polymerase, thereby extending the mRNA fragments. In some embodiments, the method comprises combining a plurality of reaction mixtures containing mRNA:cDNA hybrids, wherein the individual reaction mixtures comprise mRNA:cDNA hybrids from a plurality of cells, and then synthesizing the second strand cDNA polynucleotides from the combined mRNA:cDNA hybrids. In some embodiments, the method comprises combining a plurality of reaction mixtures containing mRNA:cDNA hybrids, wherein the individual reaction mixtures comprise mRNA:cDNA hybrids from a plurality of cells, and then contacting the combined mRNA:cDNA hybrids with an enzyme comprising RNase H activity.

In some embodiments, the method comprises combining a plurality of reaction mixtures containing mRNA:cDNA hybrids, wherein the individual reaction mixtures comprise mRNA:cDNA hybrids from a plurality of cells and wherein the mRNA is RNase H fragmented, and then contacting the combined RNase H-fragmented mRNA:cDNA hybrids with a DNA polymerase, thereby extending the mRNA fragments.

In another aspect, the present invention provides a method of sequencing a sequencing platform specific cDNA amplicon comprising: —providing the sequencing platform specific amplicon, wherein the sequencing platform specific amplicon comprises a double-stranded polynucleotide comprising: i) a first end comprising SEQ ID NO:1; ii) a second end comprising SEQ ID NO:2; and iii) a middle region comprising a double-stranded cDNA polynucleotide comprising a first strand cDNA polynucleotide complementary to an mRNA sequence hybridized to a second strand cDNA polynucleotide that corresponds to the mRNA sequence; and—sequencing the amplicon from the second end with a second sequencing primer comprising SEQ ID NO:8. In some embodiments, the first end comprises a 3' poly-A region of the second strand cDNA polynucleotide that corresponds to a 3' polyadenylation region of the mRNA sequence. In some embodiments, the second strand cDNA polynucleotide has a length that is less than 90% of the length of a corresponding mRNA.

In some embodiments, the method comprises sequencing the amplicon from the first end with a first sequencing primer and then sequencing the amplicon from the second end with the second sequencing primer. In some embodiments, the first sequencing primer comprises the sequence from 5' to 3' GCCTGTCCGCGGAAGCAGTGGTAT-CAACGCAGAGTAC (SEQ ID NO:9) or from 5' to 3' ACACTCTTTCCCTACACGACGCTCTTCCGATCT (SEQ ID NO:12). In some embodiments, the second sequencing primer comprises from 5' to 3' AGATGTGTATAAGAGACAG (SEQ ID NO:10). In some embodiments, the second sequencing primer comprises from 5' to 3' TCGTCGGCAGCGTCAGATGTGTATAAGA-GACAG (SEQ ID NO:11).

In another aspect, the present invention provides a method of sequencing a plurality of sequencing platform specific cDNA amplicons comprising: —providing the plurality of sequencing platform specific amplicons, wherein the individual sequencing platform specific amplicons comprise a double-stranded polynucleotide comprising: i) a first end comprising SEQ ID NO:1; ii) a second end comprising SEQ ID NO:2; and iii) a middle region comprising a double-stranded cDNA polynucleotide comprising a first strand cDNA polynucleotide complementary to an mRNA sequence hybridized to a second strand cDNA polynucleotide that corresponds to the mRNA sequence; —sequencing a portion of the amplicons from the second end with a second sequencing primer comprising SEQ ID NO:8; and— sequencing a portion of the amplicons from the second end with a third sequencing primer comprising from 5' to 3'GTCTCGTGGGCTCGGAGATGTGTATAAGAGACAG (SEQ ID NO:12). In some embodiments, the second sequencing primer comprises SEQ ID NO:11.

In another aspect, the present invention provides a primer comprising a 5' end and a 3' end, wherein: the 5' end comprises SEQ ID NO:2 and the 3' end comprises SEQ ID NO:8; or the 5' end comprises SEQ ID NO:1 and the 3' end comprises SEQ ID NO:7. In some embodiments, the 5' end comprises SEQ ID NO:2 and the 3' end comprises SEQ ID NO:8. In some embodiments, the primer comprises SEQ ID NO:4. In some embodiments, the 5' end comprises SEQ ID NO:1 and the 3' end comprises SEQ ID NO:7. In some embodiments, the primer comprises SEQ ID NO:5.

In another aspect, the present invention provides a kit comprising: —a first container containing a primer comprising a 5' end and a 3' end, wherein: the 5' end comprises SEQ ID NO:2 and the 3' end comprises SEQ ID NO:8; or the 5' end comprises SEQ ID NO:1 and the 3' end comprises SEQ ID NO:7; and—a second container containing a DNA polymerase.

In another aspect, the present invention provides a reaction mixture comprising: a first primer comprising SEQ ID NO:9; and a second primer comprising SEQ ID NO:11.

BRIEF DESCRIPTION OF THE DRAWINGS

FIGS. 1A and 1B illustrate various combinations of homo- (A) or heteroadapter (B) loaded tagmentases and compatible amplification primers that can be used in the methods described herein for generating cDNA sequencing libraries. FIG. 1A sequences: SEQ ID NO:12, SEQ ID NO:18, SEQ ID NO:10, SEQ ID NO:3, SEQ ID NO:16; SEQ ID NO:4, SEQ ID NO:17, SEQ ID NO:12, and SEQ ID NO:18, respectively. FIG. 1B sequences: SEQ ID NO:12, SEQ ID NO:18, SEQ ID NO:3, SEQ ID NO:16; SEQ ID NO:4, SEQ ID NO:17, SEQ ID NO:12, SEQ ID NO:18, SEQ ID NO:10, SEQ ID NO:19, and SEQ ID NO:20, respectively.

FIG. 2 illustrates various second strand synthesis schemes. "Drops" refers to steps performed in partitions (e.g., emulsion droplets). "Bulk" refers to steps performed after combining partitions. +/− ligase indicates that ligation and the use of ligase are optional.

FIG. 5 illustrates the reproducibility of the method in four different experiments across three different users and two different hydrogel particle lots.

FIG. 6b illustrates the use of homoadapter-loaded tagmentases during the tagmentation step to eliminate the mechanism of inefficient amplification of a portion of the desired adapter tagged molecules that is illustrated in FIG. 6a.

FIGS. 7a-7c illustrate a modified post-tagmentation step of PCR amplification in which a primer directed to the adapter tagged end corresponding to the 5' end of the first cDNA strand is used in combination with both a modified PCR primer (e.g., modified PCR primer 1) and a conventional PCR primer (e.g., NEXTERA PCR primer 2) to hybridize to the adapter tagged end corresponding to the 3' end of the first strand, and thereby support efficient PCR of all desired adapter tagged molecules. FIG. 7B sequences (left to right; top to bottom): SEQ ID NO:21; SEQ ID NO:13 (upside down); SEQ ID NO:12; SEQ ID NO:13 (upside down), SEQ ID NO:22, SEQ ID NO:13 (upside down), SEQ ID NO:12, SEQ ID NO:13 (upside down), SEQ ID NO:17, SEQ ID NO:23, SEQ ID NO:24 (upside down), SEQ ID NO:3, SEQ ID NO:25, SEQ ID NO:26 (upside down), SEQ ID NO:27, SEQ ID NO:28, SEQ ID NO:29 (upside down), SEQ ID NO:30, SEQ ID NO:31, and SEQ ID NO:26 (upside down). FIG. 7C sequences: SEQ ID NO:32, SEQ ID NO:33, and SEQ ID NO:34 (upside down), SEQ ID NO:19, SEQ ID NO:35 (upside down), SEQ ID NO:33, and SEQ ID NO:34 (upside down), SEQ ID NO:33, and SEQ ID NO:34 (upside down), SEQ ID NO:19, and SEQ ID NO:35 (upside down). FIG. 7C (cont.) sequences: SEQ ID NO:34, SEQ ID NO:33 (upside down), and SEQ ID NO:35, SEQ ID NO:19 (upside down), SEQ ID NO:36, SEQ ID NO:32 (upside down), SEQ ID NO:36, and SEQ ID NO:32 (upside down).

FIG. 7d illustrates a sequencing workflow for the amplification products produced in the method illustrated in FIGS. 7a-7d. FIG. 7D sequences: SEQ ID NO:9, SEQ ID NO:37, SEQ ID NO:38, SEQ ID NO:12, SEQ ID NO:18, SEQ ID NO:18, SEQ ID NO:33, SEQ ID NO:34 (upside down), SEQ ID NO:38 (upside down), SEQ ID NO:12, SEQ ID NO:19, SEQ ID NO:35 (upside down), and SEQ ID NO:37 (upside down). FIG. 7D (cont.) sequences: SEQ ID NO:9 (upside down), SEQ ID NO:36, SEQ ID NO:32 (upside down), SEQ ID NO:9 (upside down), SEQ ID NO:36, and SEQ ID NO:32 (upside down).

FIGS. 8a-8d illustrate the elimination of a post-tagmentation gap-filling prePCR step to increase the specificity of the PCR amplification reaction. FIG. 8B sequences (left to right; top to bottom): SEQ ID NO:22, SEQ ID NO:13 (upside down), SEQ ID NO:39, SEQ ID NO:13 (upside down), SEQ ID NO:22, SEQ ID NO:13 (upside down), SEQ ID NO:39, SEQ ID NO:13 (upside down), SEQ ID NO:17, SEQ ID NO:4, SEQ ID NO:33, SEQ ID NO:34 (upside down), SEQ ID NO:3, SEQ ID NO:19, SEQ ID NO:35 (upside down). FIG. 8B sequences (left to right; top to bottom): SEQ ID NO:4, SEQ ID NO:3, SEQ ID NO:32, SEQ ID NO:22, SEQ ID NO:13 (upside down), SEQ ID NO:13 (top), SEQ ID NO:22 (upside down), SEQ ID NO:39, SEQ ID NO:13 (upside down), SEQ ID NO:13 (top), SEQ ID NO:39 (upside down), SEQ ID NO:22, SEQ ID NO:13 (upside down), SEQ ID NO:36, SEQ ID NO:32 (upside down), SEQ ID NO:33, and SEQ ID NO:34 (upside down), SEQ ID NO:36, SEQ ID NO:32 (upside down), SEQ ID NO:39, SEQ ID NO:13 (upside down), SEQ ID NO:36, SEQ ID NO:32 (upside down), SEQ ID NO:19, SEQ ID NO:35 (upside down), SEQ ID NO:36, and SEQ ID NO:32 (upside down). FIG. 8D sequences: SEQ ID NO:9, SEQ ID NO:37, SEQ ID NO:38, SEQ ID NO:12, SEQ ID NO:18, SEQ ID NO:18, SEQ ID NO:33, SEQ ID NO:34 (upside down), SEQ ID NO:38 (upside down), SEQ ID NO:12, SEQ ID NO:19, SEQ ID NO:35 (upside down), and SEQ ID NO:37 (upside down). FIG. 8D (cont.) sequences: SEQ ID NO:9 (upside down), SEQ ID NO:36, SEQ ID NO:32 (upside down), SEQ ID NO:9 (upside down), SEQ ID NO:36, and SEQ ID NO:32 (upside down).

FIG. 9A sequences: SEQ ID NO:4, SEQ ID NO:37, SEQ ID NO:38, SEQ ID NO:12 and SEQ ID NO:18.

DEFINITIONS

Figure 3:
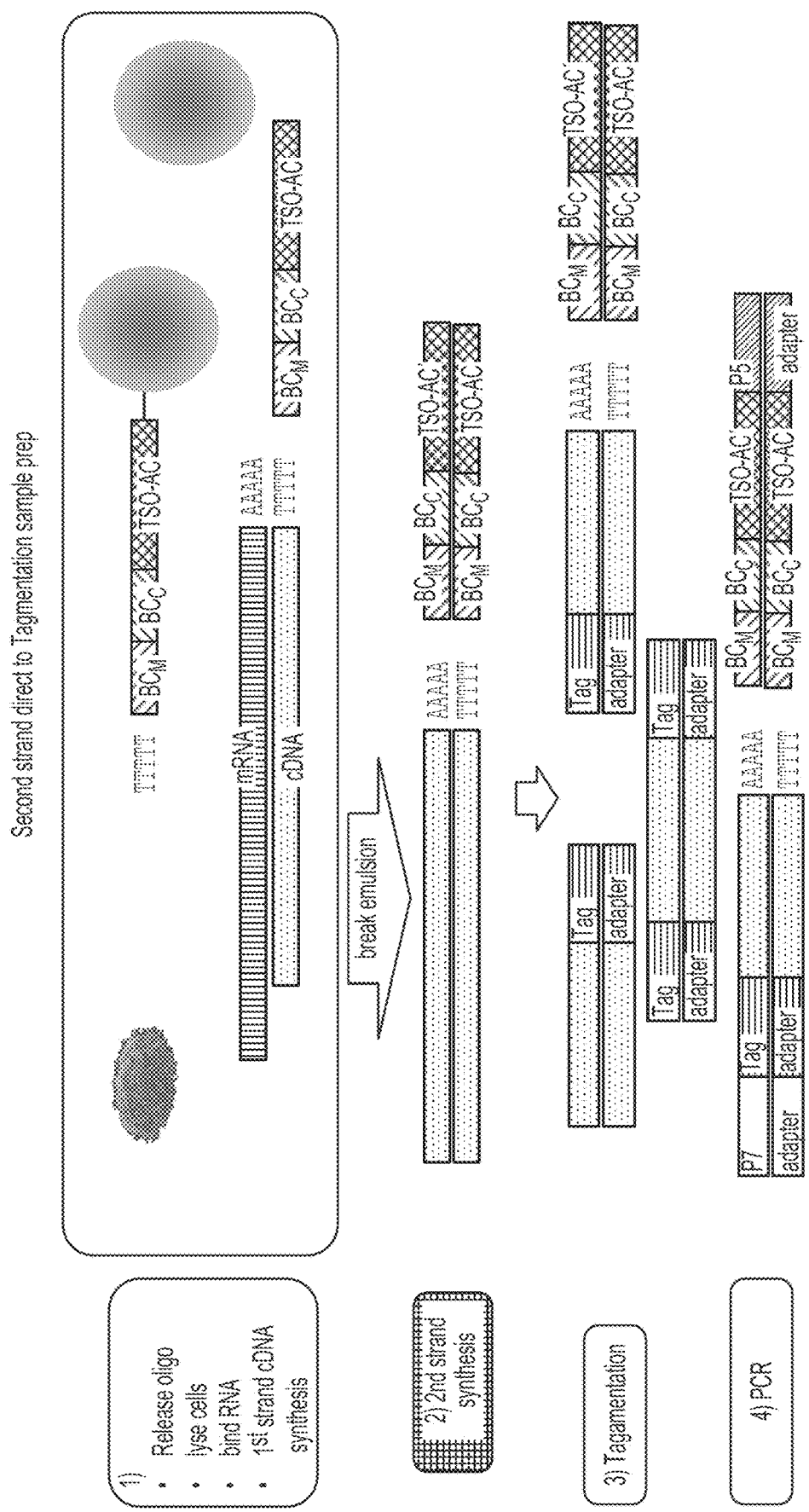
FIG. 3 illustrates a next generation sequencing workflow in which tagmentation is performed to add tag adapters (e.g., with a NEXTERA DNA Library preparation kit), and Illumina flow cell grating sequences P5 and P7 are appended to different ends of tagmentation products using PCR.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art.

The term "amplification reaction" refers to any in vitro means for multiplying the copies of a target sequence of nucleic acid in a linear or exponential manner. Such methods include but are not limited to polymerase chain reaction (PCR); DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3 SR); isothermal amplification reactions (e.g., single-primer isothermal amplification (SPIA)); as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification. In an exemplary embodiment, amplifying refers to PCR amplification using a first and a second amplification primer.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra. Primers can be DNA, RNA, or a chimera of DNA and RNA portions. In some cases, primers can include one or more modified or non-natural nucleotide bases. In some cases, primers are labeled.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is 37, 40, 42, 45, 50, 55, 60, 65, 70, 75, or 80° C.

A "template" refers to a polynucleotide sequence that comprises the polynucleotide to be amplified, flanked by or a pair of primer hybridization sites. Thus, a "target template" comprises the target polynucleotide sequence adjacent to at least one hybridization site for a primer. In some cases, a "target template" comprises the target polynucleotide sequence flanked by a hybridization site for a "forward" primer and a "reverse" primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis,* and *Thermotoga maritime,* or modified versions thereof. Additional examples of commercially available polymerase enzymes include, but are not limited to: Klenow fragment (New England Biolabs® Inc.), Taq DNA polymerase (QIAGEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.).

Polymerases include both DNA-dependent polymerases and RNA-dependent polymerases such as reverse transcriptase. At least five families of DNA-dependent DNA polymerases are known, although most fall into families A, B and C. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

As used herein, the term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

In some cases partitions are virtual. In a preferred embodiment, virtual partitions require a physical alteration of a molecule or group of molecules, wherein the alteration identifies a unique partition for that molecule or group of molecules. Typical physical alterations suitable for establishing or maintaining virtual partitioning include, without limitation, nucleic acid barcodes, detectable labels, etc. For example, a sample can be physically partitioned, and the components of each partition tagged with a unique identifier (e.g., a unique nucleic acid sequence barcode) such that the identifier is unique as compared to other partitions but shared between the components of the partition. The unique identifier can then be used to maintain a virtual partition in downstream applications that involve combining of the physically partitioned material. Thus, if the sample is a sample of cells physically partitioned into partitions containing a single cell, the identifier can identify different nucleic acids that derived from a single cell after partitions are recombined.

As used herein, a "tag" refers to a non-target nucleic acid component, generally DNA, that provides a means of addressing a nucleic acid fragment to which it is joined. For example, in preferred embodiments, a tag comprises a nucleotide sequence that permits identification, recognition, and/or molecular or biochemical manipulation of the DNA to which the tag is attached (e.g., by providing a site for annealing an oligonucleotide, such as a primer for extension by a DNA polymerase, or an oligonucleotide for capture or for a ligation reaction). The process of joining the tag to the DNA molecule is sometimes referred to herein as "tagging" and DNA that undergoes tagging or that contains a tag is referred to as "tagged" (e.g., "tagged DNA")." A tag can be a barcode or an adapter sequence.

As used herein a "barcode" is a short nucleotide sequence (e.g., at least about 4, 6, 8, 10, or 12, nucleotides long) that identifies a molecule to which it is conjugated. Barcodes can be used, e.g., to identify molecules in a partition. Such a partition-specific barcode should be unique for that partition as compared to barcodes present in other partitions. For example, partitions containing target RNA from single-cells can subject to reverse transcription conditions using primers that contain a different partition-specific barcode sequence in each partition, thus incorporating a copy of a unique "cellular barcode" into the reverse transcribed nucleic acids of each partition. Thus, nucleic acid from each cell can be distinguished from nucleic acid of other cells due to the unique "cellular barcode." In some cases, the cellular barcode is provided by a "particle barcode" that is present on oligonucleotides conjugated to a particle, wherein the particle barcode is shared by (e.g., identical or substantially identical amongst) all, or substantially all, of the oligonucleotides conjugated to that particle. Thus, cellular and particle barcodes can be present in a partition, attached to a particle, or bound to cellular nucleic acid as multiple copies of the same barcode sequence. Cellular or particle barcodes of the same sequence can be identified as deriving from the same cell, partition, or particle. Such partition-specific, cellular, or particle barcodes can be generated using a variety of methods, which methods result in the barcode conjugated to or incorporated into a solid or hydrogel support (e.g., a solid bead or particle or hydrogel bead or particle). In some cases, the partition-specific, cellular, or particle barcode is generated using a split and mix (also referred to as split and pool) synthetic scheme as described herein. A partition-specific barcode can be a cellular barcode and/or a particle barcode. Similarly, a cellular barcode can be a partition specific barcode and/or a particle barcode. Additionally, a particle barcode can be a cellular barcode and/or a partition-specific barcode.

In other cases, barcodes uniquely identify the molecule to which it is conjugated. For example, by performing reverse transcription using primers that each contain a unique "molecular barcode." In still other examples, primers can be utilized that contain "partition-specific barcodes" unique to each partition, and "molecular barcodes" unique to each molecule. After barcoding, partitions can then be combined, and optionally amplified, while maintaining virtual partitioning. Thus, e.g., the presence or absence of a target nucleic acid (e.g., reverse transcribed nucleic acid) comprising each barcode can be counted (e.g. by sequencing) without the necessity of maintaining physical partitions.

The length of the barcode sequence determines how many unique samples can be differentiated. For example, a 1 nucleotide barcode can differentiate 4, or fewer, different samples or molecules; a 4 nucleotide barcode can differentiate $4^4$ or 256 samples or less; a 6 nucleotide barcode can differentiate 4096 different samples or less; and an 8 nucleotide barcode can index 65,536 different samples or less. Additionally, barcodes can be attached to both strands either through barcoded primers for both first and second strand synthesis, through ligation, or in a tagmentation reaction.

Barcodes are typically synthesized and/or polymerized (e.g., amplified) using processes that are inherently inexact. Thus, barcodes that are meant to be uniform (e.g., a cellular, particle, or partition-specific barcode shared amongst all barcoded nucleic acid of a single partition, cell, or bead) can contain various N-1 deletions or other mutations from the canonical barcode sequence. Thus, barcodes that are referred to as "identical" or "substantially identical" copies refer to barcodes that differ due to one or more errors in, e.g., synthesis, polymerization, or purification errors, and thus contain various N-1 deletions or other mutations from the canonical barcode sequence. Moreover, the random conjugation of barcode nucleotides during synthesis using e.g., a split and pool approach and/or an equal mixture of nucleotide precursor molecules as described herein, can lead to low probability events in which a barcode is not absolutely unique (e.g., different from all other barcodes of a population or different from barcodes of a different partition, cell, or bead). However, such minor variations from theoretically ideal barcodes do not interfere with the high-throughput sequencing analysis methods, compositions, and kits described herein. Therefore, as used herein, the term "unique" in the context of a particle, cellular, partition-specific, or molecular barcode encompasses various inadvertent N-1 deletions and mutations from the ideal barcode sequence. In some cases, issues due to the inexact nature of barcode synthesis, polymerization, and/or amplification, are overcome by oversampling of possible barcode sequences as compared to the number of barcode sequences to be distinguished (e.g., at least about 2-, 5-, 10-fold or more possible barcode sequences). For example, 10,000 cells can be analyzed using a cellular barcode having 9 barcode nucleotides, representing 262,144 possible barcode sequences. The use of barcode technology is well known in the art, see for example Katsuyuki Shiroguchi, et al. Proc Natl Acad Sci USA., 2012 Jan. 24; 109(4):1347-52; and Smith, A M et al., Nucleic Acids Research Can 11, (2010). Further methods and compositions for using barcode technology include those described in U.S. 2016/0060621.

A "transposase" or "tagmentase" means an enzyme that is capable of forming a functional complex with a transposon end-containing composition and catalyzing insertion or transposition of the transposon end-containing composition into the double-stranded target DNA with which it is incubated in an in vitro transposition reaction.

The term "transposon end" means a double-stranded DNA that exhibits only the nucleotide sequences (the "transposon end sequences") that are necessary to form the complex with the transposase that is functional in an in vitro transposition reaction. A transposon end forms a "complex" or a "synaptic complex" or a "transposome complex" or a "transposome composition with a transposase or integrase that recognizes and binds to the transposon end, and which complex is capable of inserting or transposing the transposon end into target DNA with which it is incubated in an in vitro transposition reaction. A transposon end exhibits two complementary sequences consisting of a "transferred transposon end sequence" or "transferred strand" and a "non-transferred transposon end sequence," or "non transferred strand" For example, one transposon end that forms a complex with a hyperactive Tn5 transposase (e.g., EZ-Tn5™ Transposase, EPICENTRE Biotechnologies, Madison, Wis., USA) that is active in an in vitro transposition reaction comprises a transferred strand that exhibits a "transferred transposon end sequence" as follows:

(SEQ ID NO: 10)
5' AGATGTGTATAAGAGACAG 3', and a non-transferred strand that exhibits a "non-transferred transposon end sequence" as follows:

(SEQ ID NO: 13)
5' CTGTCTCTTATACACATCT 3'.

The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction.

In some embodiments, the transferred strand and non-transferred strand are covalently joined. For example, in some embodiments, the transferred and non-transferred strand sequences are provided on a single oligonucleotide, e.g., in a hairpin configuration. As such, although the free end of the non-transferred strand is not joined to the target DNA directly by the transposition reaction, the non-transferred strand becomes attached to the DNA fragment indirectly, because the non-transferred strand is linked to the transferred strand by the loop of the hairpin structure.

A "transposon end composition" means a composition comprising a transposon end (i.e., the minimum double-stranded DNA segment that is capable of acting with a transposase to undergo a transposition reaction), optionally plus additional sequence or sequences. 5'-of the transferred transposon end sequence and/or 3'-of the non-transferred transposon end sequence. For example, a transposon end attached to a tag is a "transposon end composition." In some embodiments, the transposon end composition comprises or consists of two transposon end oligonucleotides consisting of the "transferred transposon end oligonucleotide" or "transferred strand" and the "non-transferred strand end oligonucleotide," or "non-transferred strand" which, in combination, exhibit the sequences of the transposon end, and in which one or both strand comprise additional sequence.

The terms "transferred transposon end oligonucleotide" and "transferred strand" are used interchangeably and refer to the transferred portion of both "transposon ends" and "transposon end compositions," i.e., regardless of whether the transposon end is attached to a tag or other moiety. Similarly, the terms "non-transferred transposon end oligonucleotide" and "non-transferred strand" are used interchangeably and refer to the non-transferred portion of both "transposon ends" and "transposon end compositions." "In some embodiments, a transposon end composition is a "hairpin transposon end composition." As used herein, a "hairpin transposon end composition." means a transposon end composition consisting of a single oligodeoxyribonucleotide that exhibits a non-transferred transposon end sequence at its 5'-end, a transferred transposon end sequence at its 3'-end, and an intervening arbitrary sequence between the non-transferred transposon end sequence and the transferred transposon end sequence that is sufficiently long to allow intramolecular stem-loop formation, such that the transposon end portion can function in a transposition reaction. In some embodiments, the 5'-end of the hairpin transposon end composition has a phosphate group in the 5'-position of the 5'-nucleotide. In some embodiments, the intervening arbitrary sequence between the non-transferred transposon end sequence and the transferred transposon end sequence of a hairpin transposon end composition provides a tag (e.g., including one or more tag domains) for a particular use or application.

In the context of a primer sequence, an adapter sequence, a transferred strand sequence, or a tag sequence (e.g., tag attached to the 5' end of the transferred strand), the term "A" refers to an arbitrary nucleic acid sequence that is of sufficient length and sequence for selective hybridization with its reverse complement "A'." Similarly, the term "B" refers to an arbitrary nucleic acid sequence that is of sufficient length and sequence for selective hybridization with its reverse complement "B'." Similarly, the term "C" refers to an arbitrary nucleic acid sequence that is of sufficient length and sequence for selective hybridization with its reverse complement "C'." A, A', B, B', C, and C' each independently comprise or consist of a length of from about 8 to about 50 nucleotides, or more, about 10 to about 30 nucleotides, about 12 to about 24 nucleotides, or 10, 11, 12, 13, 14, 15, 16, 17, 18, 19, 20, 21, 22, 23, 24, 25, 26, 27, 28, 29, or 30 nucleotides.

Similarly, in the context of a primer sequence, an adapter sequence, a transferred strand sequence, or a tag sequence (e.g., tag attached to the 5' end of the transferred strand), the term "a" refers to an arbitrary nucleic acid sequence that is of sufficient length and sequence for selective hybridization with its reverse complement "a'." Similarly, the term "b" refers to an arbitrary nucleic acid sequence that is of sufficient length and sequence for selective hybridization with its reverse complement "b'." Similarly, the term "c" refers to an arbitrary nucleic acid sequence that is of sufficient length and sequence for selective hybridization with its reverse complement "c'." a, a', b, b', c, and c' each independently comprise or consist of a length of from about 8 to about 50 nucleotides, or more, about 10 to about 30 nucleotides, about 12 to about 24 nucleotides, or 10, 11, 12, 13, 14, 15, 16, 17, 18, 19, 20, 21, 22, 23, 24, 25, 26, 27, 28, 29, or 30 nucleotides. Moreover, a, a', b, b', c, and c' are different sequences, in at least 1, 2, 3, 4, 5, 6, 7, 8, 9, 10, 11, 12, 15, 18, or all nucleotide positions, from any sequence of A, A', B, B', C, or C'.

Similarly, in the context of a primer sequence, an adapter sequence, a transferred strand sequence, or a tag sequence (e.g., tag attached to the 5' end of the transferred strand), the term "alpha" refers to an arbitrary nucleic acid sequence that is of sufficient length and sequence for selective hybridization with its reverse complement "alpha'." Similarly, the term "beta" refers to an arbitrary nucleic acid sequence that is of sufficient length and sequence for selective hybridization with its reverse complement "beta'." Similarly, the term "delta" refers to an arbitrary nucleic acid sequence that is of sufficient length and sequence for selective hybridization with its reverse complement "delta'." alpha, alpha', beta, beta', delta, and delta' each independently comprise or consist of a length of from about 8 to about 50 nucleotides, or more, about 10 to about 30 nucleotides, about 12 to about 24 nucleotides, or 10, 11, 12, 13, 14, 15, 16, 17, 18, 19, 20, 21, 22, 23, 24, 25, 26, 27, 28, 29, or 30 nucleotides. Moreover, alpha, alpha', beta, beta', delta, and delta' are different sequences, in at least 1, 2, 3, 4, 5, 6, 7, 8, 9, 10, 11, 12, 15, 18, or all nucleotide positions, from any sequence of A, A', B, B', C, C', a, a', b, b', c, or c'. One skill in the art will appreciate that providing an example of any one of A, B, C, a, b, c, alpha, beta, or delta implicitly provides its cognate reverse complementary sequence A', B', C', a', b', c', alpha', beta', or delta'. Similarly, providing an example of any one of A', B', C', a', b', c', alpha', beta', or delta' implicitly provides its cognate reverse complementary sequence A, B, C, a, b, c, alpha, beta, or delta.

As used herein, the term "[i5]" refers to a polynucleotide that is present or absent, and when present is from 4-12 nucleotides in length that comprises an index region. In an exemplary embodiment, i5 refers to one or more, or all, of the following alternative sequences:

N501: TAGATCGC;

N502: CTCTCTAT;

N503: TATCCTCT;

N504: AGAGTAGA;

N505: GTAAGGAG;

N506: ACTGCATA;

N507: AAGGAGTA;
or

N508: CTAAGCCT.

As used herein, the term "[i7]" refers to a polynucleotide that is present or absent, and when present is from 4-12 nucleotides in length that comprises an index region. In an exemplary embodiment, i7 refers to one or more, or all, of the following alternative sequences:

N701: TAAGGCGA;

N702: CGTACTAG;

N703: AGGCAGAA;

N704: TCCTGAGC;

N705: GGACTCCT;

N706: TAGGCATG;

N707: CTCTCTAC;

N708: CAGAGAGG;

N709: GCTACGCT;

N710: CGAGGCTG;

N711: AAGAGGCA;
or

N712: GTAGAGGA.

DETAILED DESCRIPTION OF THE INVENTION

I. Introduction

Described herein are methods and compositions for transcriptome analysis. The methods can begin with reverse transcription of mRNA with a primer containing a poly-T region and a first adapter sequence (e.g., A), thereby performing first strand cDNA synthesis. The resulting first strand cDNA contains a 5' end having the first adapter sequence. Second-strand synthesis can be performed using a variety of methods known in the art that do not require that the first strand synthesis reaction reach the 5' end of the mRNA. For example, second strand synthesis can be performed by contacting the mRNA/cDNA hybrid formed by reverse transcription of the mRNA with an enzyme that possesses RNase H activity to produce an mRNA/cDNA hybrid, wherein the mRNA strand contains a plurality of mRNA fragments hybridized to the first strand cDNA molecule. The plurality of mRNA fragments can then be contacted with a DNA polymerase (e.g., a strand displacing DNA polymerase or DNA polymerase comprising 5' to 3' exonuclease activity) that is capable of extending RNA primers in a DNA template-directed polymerase reaction, thus forming a double-stranded cDNA polynucleotide, where the end of the double-stranded cDNA polynucleotide that contains the first adapter sequence comprises the 5' end of the first strand cDNA molecule and corresponds to the 3' end of the mRNA.

The enzyme that possesses RNase H activity can be the same reverse transcriptase enzyme used to perform first strand synthesis. Alternatively, the RNase H activity is provided by an enzyme that is not the reverse transcriptase enzyme used to perform first strand synthesis. For example, the RNase H activity can be a different reverse transcriptase that is contacted with the mRNA/cDNA hybrid after first strand synthesis has been initiated. Alternatively, the RNase H activity can be provided by an enzyme that is not a reverse transcriptase.

In some embodiments, second strand synthesis is performed using other methods that do not require the first strand synthesis reaction to reach the 5' end of the mRNA. Such methods include, e.g., random priming.

In such embodiments, where first strand synthesis is primed with a poly-T primer and second strand synthesis is performed with a method that is compatible with first strand synthesis reactions that do not reach the 5' end of the mRNA, the efficiency of cDNA synthesis as measured by the percent of mRNA molecules that are reverse-transcribed into a double-stranded cDNA molecule having the first adapter sequence at one end can be significantly higher than other approaches typically used to prepare cDNA libraries for high-throughput sequencing (e.g., template switching). In some cases, the efficiency can be at least 10%, at least 25%, at least 30%, at least 35%, at least 40%, at least 45%, at least 50%, at least 55%, at least 60%, at least 65%, at least 70%, or at least 75%. In some cases, the efficiency can be from about 30% to about 75%, or from about 30% to about 50%, or more.

In some cases, the efficiency as measured by the number of unique transcripts detected per cell in a high-throughput sequencing of a cDNA library produced as described herein can average (mean) as high as from 8,000 to about 15,000, or from about 4,000 to about 11,000. In some cases, the efficiency as measured by the number of genes detected per cell in a high-throughput sequencing of a cDNA library produced as described herein can average (median) as high as from 1,500 to about 6,000; or from about 1,500 to about 5,000 for a mammalian cell (e.g., human, non-human primate, rodent, rat, or mouse). In some cases, the first and second strand synthesis methods described herein are more reproducible than other methods, such as those that require first strand synthesis to the end of the template RNA strand (e.g., template switching oligonucleotide-based methods).

In such embodiments, where first strand synthesis is primed with a poly-T primer and second strand synthesis is primed with random primers or RNAs H produced mRNA fragments, only one end of the double-stranded cDNA molecule is tagged, e.g., with an adapter sequence, a cell barcode, a partition-specific barcode, a molecular barcode, or a combination of two or all thereof. However, common sequencing-platform specific workflows require a cDNA sequencing library contains an adapter sequence at both ends. Typically, the adapter sequence at each end must be different from the other. However, in some embodiments, the use of the same adapter sequence or the reverse complement thereof at both ends is compatible with the sequencing platform. Accordingly, described herein are methods of introducing a compatible adapter sequence at the other end of the double-stranded cDNA molecule. In some embodiments, the methods do not depend on the sequence of the untagged end. In an exemplary embodiment, the adapter sequence is attached to the other end of the double-stranded cDNA molecule by a tagmentase.

II. Compositions

Amplification Primers

Described herein are first (e.g., forward) and second (e.g., reverse) primers for PCR amplification of double-stranded cDNA polynucleotides that contain a first end and a second end, wherein the first end is tagged with an adapter sequence A and the complement A', and the second end is tagged with an adapter sequence B and the complement B'. Typically, the first end refers to the end that corresponds to the 3' end of the mRNA template for the cDNA molecule and the 5' end first strand cDNA molecule. In some cases, the second end of the double-stranded cDNA polynucleotide further contains an adapter sequence b and b' or c and c'.

In some embodiments, the first primer comprises the sequence A' and/or selectively hybridizes to A. In some cases, the first primer comprises the sequence A'. In an exemplary embodiment, A' comprises from 5' to 3' GCCTGTCCGCGGAAGCAGTGGTAT-CAACGCAGAGTAC (SEQ ID NO:9). In an alternative exemplary embodiment, A' comprises from the 5' to 3' at least the first 12, 13, 14, 15, 16, 17, 18 19, 20, 21, 22, 23, 24, or 25 nucleotides, or all the nucleotides of ACACTCTTTCCCTACACGACGCTCTTCCGATCT (SEQ ID NO:14). In some cases, the first primer further comprises a sequence alpha'. Typically, first primers that contain alpha' comprise from 5' to 3': alpha', A'. In some cases, alpha' comprises a sequencing platform specific adapter sequence, or the complement thereof. For example, alpha' can comprise a P5 or a P7 illumina grafting sequence (a P5 or a P7 Illumina flow cell grafting sequence). In an exemplary embodiment, alpha' comprises a P5 illumina grafting sequence from 5' to 3' AATGATACGGCGAC-CACCGAGATCTACAC (SEQ ID NO:15). In an alternative embodiment, alpha' comprises a P7 illumina grafting sequence from 5' to 3' CAAGCAGAAGACGGCAT-ACGAGAT (SEQ ID NO:2).

In some embodiments, the second primer comprises the sequence b and/or selectively hybridizes to b'. In some cases, the second primer comprises the sequence b and selectively hybridizes to b'. In an exemplary embodiment, b comprises from 5' to 3': TCGTCGGCAGCGTC (SEQ ID NO:8). In some cases, the second primer further comprises a sequence beta and/or selectively hybridizes to beta'. In some cases, the second primer comprises the sequence beta and selectively hybridizes to beta'. Typically, such second primers comprise from 5' to 3': beta, b. In some cases, beta comprises a sequencing platform specific adapter sequence, or the complement thereof. For example beta can comprise a P5 or a P7 illumina grafting sequence as described above.

In some embodiments, the second primer comprises the sequence c and/or selectively hybridizes to c'. In some cases, the second primer comprises the sequence c and selectively hybridizes to c'. In an exemplary embodiment, c comprises from 5' to 3': GTCTCGTGGGCTCGG (SEQ ID NO:7). In some cases, the second primer further comprises a sequence beta and/or selectively hybridizes to beta'. In some cases, the second primer comprises the sequence beta and selectively hybridizes to beta'. Typically, such second primers comprise from 5' to 3': beta, c. In some cases, beta comprises a sequencing platform specific adapter sequence, or the complement thereof. For example beta can comprise a P5 or a P7 illumina grafting sequence as described above.

Typically, when used as a primer pair for PCR amplification first and second primers comprise different sequencing platform specific adapter sequences. For example, when the first primer comprises a P5 grafting sequence, the second primer can comprise a P7 grafting sequence. As yet another example, when the first primer comprises a P7 grafting sequence, the second primer can comprise a P5 grafting sequence. Thus, cDNA polynucleotides amplified with such first and second primers can contain two different grafting sequences, one on each end. For example, the amplified cDNA can contain a P5 sequence at one end (e.g., the first end) and a P7 drafting sequence at another end (e.g., the second end). As yet another example, the amplified cDNA can contain a P7 sequence at the first end and a P5 grafting sequence at the second end.

As further described below, second amplification primers that contain b and second amplification primers that contain c can be used simultaneously in a reaction mixture with first amplification primers described herein. Such reaction mixtures are useful, e.g., where at least two different cDNA polynucleotides are present or can be present, where a first cDNA polynucleotide can be amplified with a first amplification primer as described herein and a second amplification primer that contains b, and the second cDNA polynucleotide can be amplified with a first amplification primer as described herein and a second amplification primer that contains c. As used herein, where one first amplification primer and two different second amplification primers are provided or used, one of the two different second amplification primers can be referred to as a third amplification primer. Such a reaction mixture can be generated, e.g., using a heteroadapter loaded tagmentase or two differently loaded homoadapter loaded tagmentases as described herein.

In some embodiments, an amplification primer comprising a 5' end and a 3' end is provided herein, wherein the 5' end comprises SEQ ID NO:2 and the 3' end comprises SEQ ID NO:8; or the 5' end comprises SEQ ID NO:1 and the 3' end comprises SEQ ID NO:7. In some cases, the 5' end comprises SEQ ID NO:2 and the 3' end comprises SEQ ID NO:8. In some cases, the 5' end comprises SEQ ID NO:1 and the 3' end comprises SEQ ID NO:7.

Additional amplification primers useful in the methods and compositions described herein include, but are not limited to the following: an amplification primer that comprises from 5' to 3':

(SEQ ID NO: 15)
AATGATACGGCGACCACCGAGATCTACAC;

(SEQ ID NO: 2)
CAAGCAGAAGACGGCATACGAGAT;

(SEQ ID NO: 3)
CAAGCAGAAGACGGCATACGAGAT[i7]GTCTCGTGGGCTCGG;

(SEQ ID NO: 4)
CAAGCAGAAGACGGCATACGAGAT[i7]TCGTCGGCAGCGTC;

(SEQ ID NO: 16)
AATGATACGGCGACCACCGAGATCTACAC[i5]GTCTCGTGGGCTCGG;

(SEQ ID NO: 17)
AATGATACGGCGACCACCGAGATCTACAC[i5]TCGTCGGCAGCGTC;

(SEQ ID NO: 12)
GTCTCGTGGGCTCGGAGATGTGTATAAGAGACAG;

(SEQ ID NO: 18)
TCGTCGGCAGCGTCAGATGTGTATAAGAGACAG;

(SEQ ID NO: 10)
AGATGTGTATAAGAGACAG;

(SEQ ID NO: 19)
CAAGCAGAAGACGGCATACGAGAT[i7]GTCTCGTGGGCTCGGAGA

TGTGTATAAGAGACAG;

(SEQ ID NO: 20)
AATGATACGGCGACCACCGAGATCTACAC[i5]TCGTCGGCAGCGTCA

GATGTGTATAAGAGACAG.

FIGS. 1A and 1B illustrate various illustrative combinations of two or more of the above amplification primers, and corresponding transferred ends that can be used in the methods of the present invention.

Tagmentases

Described herein are heteroadapter loaded tagmentases and homoadapter loaded tagmentases, as well as compositions and methods for using such tagmentases. Homoadapter loaded tagmentases are tagmentases that contain a single transferred strand sequence. Thus, contacting a target polynucleotide (e.g., double-stranded cDNA) with a homoadapter loaded tagmentase covalently links a single species of transferred strand to the 5' end of a fragment produced by the tagmentase enzyme. In some embodiments, homoadapter loaded tagmentases are used in a reaction mixture that does not contain a differently loaded tagmentase (e.g., does not contain a different homoadapter loaded tagmentase and does not contain a heteroadapter loaded tagmentase). In such a reaction mixture, the transferred strand is the same for every product of a tagmentation reaction.

Heteroadapter loaded tagmentases are tagmentases that contain two different transferred strands, where one of the two transferred strands is transferred in the tagmentation reaction. Thus, contacting a target polynucleotide (e.g., double-stranded cDNA) with a heteroadapter loaded tagmentase covalently links either of two species of transferred strand to the 5' end of a fragment produced by the tagmentase enzyme. In some embodiments, heteroadapter loaded tagmentases are used in a reaction mixture to transfer the one of the two different transferred strands to the target polynucleotides in the reaction mixture. Thus, target polynucleotides will be tagged with either transferred strand or both of the heteroadapter loaded tagmentase. Similarly, two different homoadapter loaded tagmentases can be used in a reaction mixture to achieve the same transfer of two different transferred strands to target polynucleotides.

Adapter loaded tagmentases are further described, e.g., in U.S. Patent Publication Nos: 2010/0120098; 2012/0301925; and 2015/0291942 and U.S. Pat. Nos. 5,965,443; 6,437,109;

7,083,980; 9,005,935; and 9,238,671, the contents of each of which are hereby incorporated by reference in the entirety for all purposes.

In some embodiments, the homoadapter loaded tagmentase comprises a transferred strand comprising the sequence B and/or selectively hybridizes to B'. In some embodiments, the homoadapter loaded tagmentase comprises the sequence B and selectively hybridizes to B'. In an exemplary embodiment, the homoadapter loaded tagmentase comprises a transferred strand comprising or consisting of B, wherein B has the following sequence from 5' to 3': AGATGTGTATAAGAGACAG (SEQ ID NO:10). In some embodiments, the transferred strand of the homoadapter loaded tagmentase further comprises the sequence b and/or selectively hybridizes to b'. In some embodiments, the transferred strand of the homoadapter loaded tagmentase further comprises the sequence b and selectively hybridizes to b'. In an exemplary embodiment, the homoadapter loaded tagmentase comprises a transferred strand comprising or consisting of b, wherein b has the following sequence from 5' to 3': TCGTCGGCAGCGTC (SEQ ID NO:8). In some cases, the homoadapter loaded tagmentase comprises a transferred strand that comprises or consists of from 5' to 3': b, B. In some cases, the homoadapter loaded tagmentase comprises a transferred strand that comprises or consists of from 5' to 3': b, B, wherein b, B has the sequence from 5' to 3': TCGTCGGCAGCGTCAGATGTGTATAAGAGACAG (SEQ ID NO:18).

In some embodiments, the transferred strand of the homoadapter loaded tagmentase comprising B and/or a sequence that selectively hybridizes to B' further comprises the sequence c and/or selectively hybridizes to c'. In some embodiments, the homoadapter loaded tagmentase further comprises the sequence c and selectively hybridizes to c'. In an exemplary embodiment, the homoadapter loaded tagmentase comprises a transferred strand comprising or consisting of c, wherein c has the following sequence from 5' to 3': GTCTCGTGGGCTCGG (SEQ ID NO:7). In some cases, the homoadapter loaded tagmentase comprises or consists from 5' to 3': c, B. In some cases, the homoadapter loaded tagmentase comprises a transferred strand that comprises or consists of from 5' to 3': c, B, wherein c, B has the sequence from 5' to 3': GTCTCGTGGGCTCGGAGATGTGTATAAGAGACAG (SEQ ID NO:12).

Heteroadapter loaded tagmentases comprise a first and second transferred strand, wherein the first transferred strand is different from the second transferred strand. However, ins some embodiments, the different transferred strands contain regions that are identical or substantially identical. For example, the heteroadapter loaded tagmentase can comprise a first and second transferred strand where each first and second transferred strand comprises B or a sequence that selectively hybridizes to B'. In some cases, the heteroadapter loaded tagmentase comprises a first and second transferred strand where each first and second transferred strand comprises B. In an exemplary embodiment, the heteroadapter loaded tagmentases comprise a first and second transferred strand where each first and second transferred strand comprises B, wherein B has the sequence from 5' to 3': AGATGTGTATAAGAGACAG (SEQ ID NO:10).

Typically, the transferred strand of the heteroadapter loaded tagmentase further comprises a tag at the 5' end of the transferred strand that differs between the first and second transferred strand. In some embodiments, the heteroadapter loaded tagmentase comprises a first and second transferred strand, wherein the first transferred strand comprises the sequence b or a sequence that selectively hybridizes to b', and the second transferred strand comprises the sequence c or a sequence that selectively hybridizes to c'. Thus, in some embodiments, the heteroadapter loaded tagmentase can comprise a first transferred strand comprising from 5' to 3': b, B; and a second transferred strand comprising from 5' to 3': c, B. In some cases, the heteroadapter loaded tagmentase comprises a first transferred strand that comprises or consists of from 5' to 3': b, B, wherein b, B has the sequence from 5' to 3': TCGTCGGCAGCGTCAGATGTGTATAAGAGACAG (SEQ ID NO:18). In some cases, the heteroadapter loaded tagmentase comprises a second transferred strand that comprises or consists from 5' to 3': c, B, wherein c, B has the sequence from 5' to 3': GTCTCGTGGGCTCGGAGATGTGTATAAGAGACAG (SEQ ID NO:12).

Partitions

In some embodiments, a sample is partitioned and one or more of cell lysis, first strand synthesis, second strand synthesis, or first and second strand synthesis is performed in the partitions. In some cases, the sample is a sample of cells, and cells are partitioned such that each partition contains no more than a single cell. In some cases, the sample is a sample of cells, and cells are partitioned such that at least 90%, 95%, 99%, or more partitions contain no more than a single cell. In some cases, the cells are partitioned such that the average number of cells in a partition is 1. In some cases, the cells are partitioned such that the average number of cells in a partition is from 10 to 1,000 cells, from 25 to 500 cells, from 50 to 500 cells, or from 50 to 200 cells. In some cases, the sample is a sample of mRNA and the mRNA is partitioned such that, on average, mRNA from 10 to 1,000 cells, from 25 to 500 cells, from 50 to 500 cells, or from 50 to 200 cells is present in the partitions.

In some embodiments, the sample is partitioned into a sufficient number of partitions such that all, substantially all, or at least a majority of partitions have no more than 5 cells (e.g., about 1, 2, 3, 4, or 5 cells), or mRNA therefrom. In some embodiments, the sample is partitioned into a sufficient number of partitions such that all, substantially all, or at least a majority of partitions have no more than 1 cell or mRNA therefrom. In some embodiments, on average no more than 5, 4, 3, 2, 1, 0.75, 0.5, 0.4, 0.3, 0.2, 0.1, or 0.05 cells are present in each partition. In some embodiments, on average about 0.05, 0.1, 0.2, 0.3, 0.4, 0.5, 0.75, 1, 2, 3, 4, or 5 cells are present in each partition. In some embodiments, in a population of partitions containing cells, the mode number of cells in a partition is 1, or is 0.

Methods and compositions for partitioning a sample (e.g., a sample of cells or a sample of mRNA) are described, for example, in published patent applications WO 2010/036,352, US 2010/0173,394, US 2011/0092,373, and US 2011/0092,376, the contents of each of which are incorporated herein by reference in the entirety. The plurality of mixture partitions can be in a plurality of emulsion droplets, or a plurality of microwells, etc.

Cells can be partitioned into a plurality of mixture partitions, lysed in the partitions, and first strand synthesis can be performed therein. Similarly mRNA can be partitioned prior to first strand synthesis. For example, mRNA can be partitioned into a plurality of mixture partitions and first strand synthesis can be performed therein. As another example, first strand cDNA (e.g., as single-stranded cDNA or as an mRNA/cDNA hybrid) can be partitioned and second strand synthesis performed therein.

In some embodiments, cells, mRNA, or first and/or second strand cDNA, etc. can be partitioned into a plurality of mixture partitions, and then one or more amplification primer(s), probe(s), enzyme(s), oligonucleotides, beads, barcodes, or a combination thereof, can be introduced into the plurality of mixture partitions. Methods and compositions for delivering reagents (e.g., probes, enzymes, primers, barcodes, oligonucleotides, salts, buffers, divalent cations, etc.) to one or more mixture partitions include microfluidic methods as known in the art; droplet or microcapsule merging, coalescing, fusing, bursting, or degrading (e.g., as described in U.S. 2015/0027,892; US 2014/0227,684; WO 2012/149,042; and WO 2014/028,537); droplet injection methods (e.g., as described in WO 2010/151,776); and combinations thereof.

As described herein, the mixture partitions can be picowells, nanowells, or microwells. The mixture partitions can be pico-, nano-, or micro-reaction chambers, such as pico, nano, or microcapsules. The mixture partitions can be pico-, nano-, or micro-channels. The mixture partitions can be droplets, e.g., emulsion droplets.

In an exemplary embodiment, cells are partitioned into mixture partitions containing oligo-dT primers that further contain one or more, or all, of a partition-specific barcode (e.g., a cell barcode when the partition contains a single cell), a molecular barcode, and an adapter sequence A or A'. Cells are lysed to release mRNA, and first strand synthesis is performed therein. Thus, a partition can contain a cell or plurality of cells (e.g., 10-1,000, 25 to 500, 50 to 500, or 50 to 200 cells) or mRNA therefrom, an oligo-dT primer containing one or more, or all, of a partition-specific barcode (e.g., a cell barcode when the partition contains a single cell), a molecular barcode, and an adapter sequence A or A', and a reverse transcriptase (e.g., a reverse transcriptase that comprises RNase H activity or a reverse transcriptase that lacks or substantially lacks RNase H activity). In some cases, the partition contains oligo-dT primer that is coupled to a solid or hydrogel support. In some cases, the link between the oligo-dT primer and the solid or hydrogel support can be cleaved by heating the hydrogel to a temperature that melts the support or contacting the solid support with a cleavage agent. Thus, in some embodiments, the partition contains a cleaving agent, such as a thiol or one or more enzymes. In some cases, the enzyme is a restriction enzyme. In some cases, the one or more enzymes comprise uracil DNA glycosylase, DNA glycosylase-lyase Endonuclease VIII, or a combination thereof.

In some embodiments, the partitions are droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes. In some cases, such stability or minimal coalescence is maintained for up to 4, 6, 8, 10, 12, 24, or 48 hours or more (e.g., at room temperature, or at about 0, 2, 4, 6, 8, 10, or 12° C.). In some embodiments, the droplet is formed by flowing an oil phase through an aqueous sample comprising the cells, mRNA, or cDNA.

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H, 2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can be removed prior to heating, or left in place. The microcapsules can be resistant to coalescence and/or flocculation across a wide range of thermal and mechanical processing.

Following conversion of droplets into microcapsules, the microcapsules can be stored at about −70°, 20°, 0°, 3°, 4°, 5°, 6°, 7°, 8°, 9°, 10°, 15°, 20°, 25°, 30°, 35°, or 40° C. In some embodiments, these capsules are useful for storage or transport of partition mixtures. For example, samples can be collected at one location, partitioned into droplets containing enzymes, buffers, and/or primers or other probes, optionally one or more polymerization reactions can be performed, the partitions can then be heated to perform microencapsulation, and the microcapsules can be stored or transported for further analysis.

In some embodiments, the sample is partitioned into, or into at least, 500 partitions, 1000 partitions, 2000 partitions, 3000 partitions, 4000 partitions, 5000 partitions, 6000 partitions, 7000 partitions, 8000 partitions, 10,000 partitions, 15,000 partitions, 20,000 partitions, 30,000 partitions, 40,000 partitions, 50,000 partitions, 60,000 partitions, 70,000 partitions, 80,000 partitions, 90,000 partitions, 100,000 partitions, 200,000 partitions, 300,000 partitions, 400,000 partitions, 500,000 partitions, 600,000 partitions, 700,000 partitions, 800,000 partitions, 900,000 partitions, 1,000,000 partitions, 2,000,000 partitions, 3,000,000 partitions, 4,000,000 partitions, 5,000,000 partitions, 10,000,000 partitions, 20,000,000 partitions, 30,000,000 partitions, 40,000, 000 partitions, 50,000,000 partitions, 60,000,000 partitions, 70,000,000 partitions, 80,000,000 partitions, 90,000,000 partitions, 100,000,000 partitions, 150,000,000 partitions, or 200,000,000 partitions.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

Reaction Mixtures

Described herein are reaction mixtures for preparing a high-throughput sequencing cDNA library. In one aspect, a reaction mixture is produced by combining a plurality of mixture partitions. For example, mixture partitions can be combined after first strand synthesis or after second strand synthesis to generate a reaction mixture. In some cases, the reaction mixture contains a plurality of mRNA/cDNA hybrids or double-stranded cDNAs, that each comprise a sequence A' at the 5' end of the first strand cDNA. In some cases, A' comprises from 5' to 3': GCCTGTCCGCG-GAAGCAGTGGTATCAACGCAGAGTAC (SEQ ID NO:9). In some cases, the reaction mixture contains a plurality of mRNA/cDNA hybrids or double-stranded cDNAs, that each comprise a sequence A' at the 5' end of the first strand cDNA, and also a partition-specific barcode (e.g., a cell barcode), or a molecular barcode, or a partition-specific barcode and a molecular barcode.

In some cases, the reaction mixture comprises reagents for second strand synthesis. In some cases, the reagents include an RNase H. In some cases, the reagents include a strand-displacing DNA-dependent DNA polymerase. In some cases, the reagents include a DNA-dependent DNA polymerase capable of extending mRNA fragment primers. In some cases, the DNA-dependent DNA polymerase comprises 5' to 3' exonuclease activity. In an exemplary embodiment, the DNA-dependent DNA polymerase is *E. coli* DNA Polymerase I. In some cases, the reaction mixture comprises random primers, such as random hexamer or random decamer primers.

In some cases, the reagents for second strand synthesis further comprise a ligase. For example, the ligase can be a thermophilic ligase. For example, the ligase can be Taq ligase, or 9° N ligase. Alternatively, the ligase can be a mesophilic ligase, such as *E. coli* DNA ligase, or T4 DNA ligase.

In some cases, the reaction mixture comprises a homoadapter loaded tagmentase, such as one of the homoadapter loaded tagmentases described herein. In some cases, the reaction mixture does not contain other tagmentases that are differentially loaded. In other embodiments, the reaction mixture comprises a heteroadapter loaded tagmentase as described herein. Generally the reaction mixture further comprises reagents and conditions suitable for performing a tagmentation reaction to transfer the transferred strand of the tagmentase to the 5' end of a second strand cDNA molecule (e.g., in a double-stranded cDNA) present in the reaction mixture.

In some cases, the reaction mixture contains tagmentation products produced under such conditions. For example, the reaction mixture can contain a double-stranded cDNA polynucleotide containing a sequence A at a first end and a sequence B at a second end. In some cases, the second end further comprises b or c. In some cases, the reaction mixture comprises a plurality of cDNA polynucleotides containing sequence A at a first end and sequence b, B at the second end, and a plurality of cDNA polynucleotides containing sequence A at the first end and sequence c, B at the second end.

In some cases, the reaction mixture can contain primers for PCR amplification of double-stranded cDNA polynucleotides containing adapter A at a first end and adapter B (e.g., b,B or c,B) at a second end. For example, the amplification primers can be a two primer pair in which a first primer selectively hybridizes to A and a second primer selectively hybridizes to b'. Alternatively, the amplification primers can be a two primer pair in which a first primer selectively hybridizes to A and a second primer selectively hybridizes to c'. As yet another alternative, the amplification primers can be a three primer mixture in which a first primer selectively hybridizes to A, a second primer selectively hybridizes to b', and a third primer selectively hybridizes to c'.

The amplification primers can further contain grafting sequences. For example, the first amplification primer can contain a grafting sequence alpha or alpha'. As another example, the second amplification primer can contain a grafting sequence beta or beta'. As yet another example, the second and third amplification primers (i.e., the two different second amplification primers) each independently contain a grafting sequence beta or beta'. As yet another example, the second and third amplification primers can each contain the same grafting sequence, whether beta or beta'. The amplification primers can contain the grafting sequence at the 5' end and the selectively hybridizing sequence at a 3' end. In some cases, the grafting sequence, or a portion thereof is not present in the first, second, or third amplification primer, two or all thereof. For example, a partial grafting sequence, or no grafting sequence can be added in a first double-stranded cDNA amplification step, and a full grafting sequence can be added by amplifying with another set of amplification primers. As such, the reaction mixture can contain at least two additional (e.g., forward and reverse) amplification primers.

In some embodiments, it can be advantageous to reduce or eliminate the "gap-filling" by one or more DNA-dependent DNA polymerase in a reaction mixture containing amplification primers and tagmentase products. For example, increased specificity can be achieved by reducing or eliminating extension of the 3' end of the first strand cDNA molecule (e.g., templated by the transferred strand attached to the 5' end of the second strand cDNA molecule that is hybridized to the first strand cDNA) prior to the first cycle of PCR amplification with the amplification primers. Accordingly, in some examples, the reaction mixture is held at a temperature that is not permissive for polymerase-mediated extension (e.g., 0, 4, 8, 10, 15, or 25° C.) until the reaction mixture is transferred to conditions suitable for a denaturation step (e.g., 90, or 95° C.) in a PCR reaction. Alternatively, or additionally, the reaction mixture can contain a hot-start DNA polymerase, or contain a hot-start DNA polymerase and no other substantial DNA polymerase enzyme activity. Thus, polymerase mediated extension substantially occurs after the initial denaturing step of PCR. Additionally, or alternatively, an essential component of an amplification reaction (e.g., the polymerase) can be added to the reaction mixture after it has been equilibrated to a denaturing temperature.

In some embodiments, a reaction mixture is provided for sequencing a tagged double-stranded cDNA polynucleotide that contains a grafting sequence alpha at one end and a grafting sequence beta at a second end. In some cases, the end containing the grafting sequence beta of the tagged double-stranded cDNA polynucleotides in the reaction mixture further contains either sequence b or c, e.g., wherein b or c is 3' to beta. In some cases, the end of the tagged double-stranded cDNA polynucleotides in the reaction mixture that contains the grafting sequence beta further contains sequence B, wherein B is 3' to beta. In some cases, the end of the tagged double-stranded cDNA polynucleotides in the reaction mixture that contains the grafting sequence beta further contains sequence either b or c, in combination with B, wherein b or c is 3' to beta, and B is 3' to both beta and b or c. In some embodiments, therefore a mixture for sequencing the double-stranded cDNA polynucleotides can contain a read primer comprising from 5' to 3': b, B; and a second read primer comprising from 5' to 3': c, B. In some cases, the read primer comprising from 5' to 3': b, B, comprises the sequence from 5' to 3': TCGTCGGCAGCGTCAGATGTGTATAAGAGACAG (SEQ ID NO:18). In some cases, the read primer comprising from 5' to 3': c, B, comprises the sequence from 5' to 3': GTCTCGTGGGCTCGGAGATGTGTATAAGAGACAG (SEQ ID NO:12).

III. Methods

Described herein are methods for tagging a cDNA polynucleotide. The methods can be useful for, e.g., preparing a cDNA sequencing library. In one aspect, the method includes: providing a double-stranded mRNA:cDNA hybrid comprising a first strand cDNA polynucleotide having a 5' end and a 3' end and hybridized to a complementary mRNA having a 5' end and a 3' end, wherein the 5' end of the first strand cDNA polynucleotide comprises a first adapter sequence (e.g., A) or complement thereof. In some embodiments, the double-stranded RNA:cDNA hybrid is provided by contacting the mRNA with a reverse transcriptase and a first strand synthesis primer to thereby extend the first strand synthesis primer in an mRNA template-directed DNA polymerase reaction, wherein the first strand synthesis primer comprises a 3' oligo-dT end region and a 5' end comprising the first adapter sequence (e.g., A) or complement thereof, thereby synthesizing the first strand cDNA polynucleotide hybridized to the complementary mRNA, and wherein the 5' end of the first strand cDNA comprises the first adapter sequence (e.g., A) or complement thereof.

In some embodiments, the first strand synthesis primer further comprises a molecular barcode, a cell or partition-specific barcode, or a combination thereof. In some cases, the first strand synthesis is performed in a mixture partition, such as an emulsion droplet or a micro- or nanowell. In some cases, the method includes partitioning a sample (e.g., cells or mRNA), lysing cells in the mixture partitions if present, and performing first strand synthesis. In some cases, the sample is partitioned into a set of partitions containing the first strand synthesis primers (e.g., linked to a solid or hydrogel support). In some cases, the sample is partitioned into a set of partitions, and then the first strand synthesis primers (e.g., linked to a solid or hydrogel support) are partitioned into the partitions.

In some embodiments, the first strand synthesis is performed under conditions that are likely to generate a significant number of mRNA:cDNA hybrid polynucleotides where the first strand synthesis did not proceed to the 5'-most nucleotide of the mRNA. Such products are characterized by having a single-stranded 5'-mRNA end. In some cases, a plurality of first strand synthesis reactions are performed, e.g., in a plurality of mixture partitions, under conditions such that at least 25%, 30%, 45%, 50%, 55%, 60%, 65%, 70%, 75%, 80%, 85%, 90%, or more of the mRNA:cDNA hybrids comprise a 5' mRNA end that is single-stranded. In some cases, a plurality of first strand synthesis reactions are performed, e.g., in a plurality of mixture partitions, such that at least 25% to 90%, 30%-80%, or 45%-60% of the mRNA:cDNA hybrids comprise a 5' mRNA end that is single-stranded. Alternatively, first strand synthesis can be performed under conditions that promote completion of the reaction, such that the 5' mRNA end of the resulting mRNA:cDNA hybrids is predominantly double-stranded.

In some embodiments, where first strand synthesis is performed in partitions, partitions are combined after first strand synthesis and before second strand synthesis. In some embodiments, first stand and second strand synthesis is performed in partitions, and then partitions are combined. FIG. 2 illustrates several alternative embodiments for performing first strand synthesis in emulsion droplet partitions ("drops"), and performing second strand synthesis either in bulk (after combining partitions) or in the partitions.

In some embodiments, synthesizing second strand cDNA polynucleotides is performed by i) contacting the mRNA:cDNA hybrid with an enzyme comprising RNase H activity, thereby producing mRNA fragments hybridized to the first strand cDNA, and ii) contacting the mRNA fragments with a DNA polymerase, thereby extending the mRNA fragments in a template-directed polymerase reaction, wherein the template is the first strand cDNA polynucleotide and forming a double-stranded cDNA polynucleotide. In some cases, the double-stranded cDNA polynucleotide is contacted with a ligase to join second strand cDNA fragments. In some cases, the RNase H activity is provided by the same enzyme used in the first strand synthesis reaction. In some cases, the reverse transcriptase used in first strand synthesis does not comprise RNase H activity, or does not comprise sufficient RNase H activity, and a distinct RNase H enzyme is used. In some cases, the RNase H digestion of mRNA hybridized to the first strand is performed in the partitions (e.g., where the reverse transcriptase comprises RNase H activity). In some case, the RNase H digestion of mRNA hybridized to the first strand is performed in bulk (e.g., wherein an RNase H enzyme that is not the reverse transcriptase used in first strand synthesis is provided in the bulk reaction mixture).

In some cases, second strand cDNA synthesis is performed with a polymerase that extends from an RNA primer and comprises 5' to 3' exonuclease activity. In some cases, second strand cDNA synthesis is performed with a polymerase that extends from an RNA primer and comprises strand-displacement activity.

In some embodiments the method comprises contacting the one or more double-stranded cDNA polynucleotides produced in the first and second strand synthesis reactions described above with an adapter-loaded tagmentase, thereby forming a reaction mixture comprising a tagged double-stranded cDNA polynucleotide comprising a first end and a second end, wherein the first end comprises the first adapter sequence (e.g., A) and complement thereof, and the second end comprises a second adapter sequence (e.g., B; b,B; or c,B, or a mixture of cDNAs containing b,B or c,B) and complement thereof.

In some cases, the contacting of the double-stranded cDNA polynucleotide with the adapter-loaded tagmentase is performed in a reaction mixture that contains a homo adapter-loaded tagmentase and does not contain adapter-loaded tagmentases having a different adapter. In such embodiments, where a plurality of double-stranded cDNA polynucleotides are contacted with the homo adapter-loaded tagmentase (e.g., loaded with a transferred strand comprising B; b,B; or c,B), each double-stranded cDNA polynucleotide comprising the first end (e.g., A) comprises a shared second end (e.g., B; b,B; or c,B, but not a mixture thereof).

In some cases, the contacting of the double-stranded cDNA polynucleotide with the adapter-loaded tagmentase is performed in a reaction mixture that contains two different homo adapter-loaded tagmentases or a heteroadapter loaded tagmentase. In such embodiments, where a plurality of double-stranded cDNA polynucleotides are contacted with the heteroadapter-loaded tagmentase (e.g., loaded with a transferred strand comprising b,B; and c,B), each double-stranded cDNA polynucleotide comprising the first end (e.g., A) comprises one of two second ends (e.g., b,B; or c,B). Similarly, in such embodiments where a first homo-adapter loaded tagmentase (e.g., loaded with a transferred strand comprising b,B) and a second homoadapter loaded tagmentase (e.g., loaded with a transferred strand comprising c,B) are contacted with a plurality of double-stranded cDNA polynucleotides, each double-stranded cDNA polynucleotide comprising the first end (e.g., A) comprises one of two second ends (e.g., b,B; or c,B).

In some embodiments, the method further comprises selectively amplifying from the reaction mixture the one or more tagged double-stranded cDNA polynucleotides by contacting the tagged double-stranded cDNA polynucleotides with a first amplification primer and a second amplification primer, wherein the first amplification primer selectively hybridizes to the first adapter sequence (e.g., A') or its complement (e.g., A') and comprises a first sequencing-platform-specific adapter sequence (e.g., alpha) or its complement (e.g., alpha'), and wherein the second amplification primer selectively hybridizes to the second adapter sequence (b' or c') and comprises a second sequencing-platform-specific adapter sequence (e.g., a grafting sequence), thereby producing a sequencing platform-specific cDNA amplicon. In some cases, the second sequencing-platform-specific adapter sequence comprises sequence beta.

Exemplary Homoadapter Tagmentase Reactions

In some embodiments, the tagmentase is a homoadapter-loaded tagmentase that is loaded with the transferred strand comprising the sequence from 5' to 3': GTCTCGTGGGCTCGGAGATGTGTATAAGAGACAG (SEQ ID NO:12), and the second amplification primer comprises from 5' to 3': CAAGCAGAAGACGGCATACGAGAT[i7]GTCTCGTGGGCTCGG (SEQ ID NO:3). The first amplification primer selectively hybridizes to A or A' and contains the grafting sequence alpha (e.g., from 5' to 3' AATGATACGGCGACCACCGAGATCTACAC (SEQ ID NO:15)). With reference to FIG. 1, this refers to "version 1." In some embodiments, the tagmentase is a homoadapter-loaded tagmentase that is loaded with the transferred strand comprising the sequence from 5' to 3': GTCTCGTGGGCTCGGAGATGTGTATAAGAGACAG (SEQ ID NO:12), and the second amplification primer comprises from 5' to 3': AATGATACGGCGAC-CACCGAGATCTACAC[i5]GTCTCGTGGGCTCGG (SEQ ID NO:16). The first amplification primer selectively hybridizes to A or A' and contains the grafting sequence alpha (e.g., from 5' to 3' CAAGCAGAAGACGGCATACGAGAT (SEQ ID NO:2)). With reference to FIG. 1, this refers to "version 2."

In some embodiments, the tagmentase is a homoadapter-loaded tagmentase that is loaded with the transferred strand comprising the sequence from 5' to 3': TCGTCGGCAGCGTCAGATGTGTATAAGAGACAG (SEQ ID NO:18), and the second amplification primer comprises from 5' to 3': CAAGCAGAAGACGGCATACGAGAT[i7]TCGTCGGCAGCGTC (SEQ ID NO:4). The first amplification primer selectively hybridizes to A or A' and contains the grafting sequence alpha (e.g., from 5' to 3' AATGATACGGCGACCACCGAGATCTACAC (SEQ ID NO:15)). With reference to FIG. 1, this refers to "version 3." In some embodiments, the tagmentase is a homoadapter-loaded tagmentase that is loaded with the transferred strand comprising the sequence from 5' to 3': TCGTCGGCAGCGTCAGATGTGTATAAGAGACAG (SEQ ID NO:18), and the second amplification primer comprises from 5' to 3': AATGATACGGCGAC-CACCGAGATCTACAC[i5]TCGTCGGCAGCGTC (SEQ ID NO:17). The first amplification primer selectively hybridizes to A or A' and contains the grafting sequence alpha (e.g., from 5' to 3' CAAGCAGAAGACGGCATACGAGAT (SEQ ID NO:2)). With reference to FIG. 1, this refers to "version 4."

In some embodiments, the tagmentase is a homoadapter-loaded tagmentase that is loaded with the transferred strand comprising the sequence from 5' to 3': AGATGTGTATAAGAGACAG (SEQ ID NO:10), and the second amplification primer comprises from 5' to 3': GTCTCGTGGGCTCGGAGATGTGTATAAGAGACAG (SEQ ID NO:12). In this embodiment, an "outer" amplification primer is used to attach a grafting sequence to the end of the cDNA comprising the transferred strand. The "outer" amplification primer can comprise from 5' to 3': CAAGCAGAAGACGGCATACGAGAT[i7] GTCTCGTGGGCTCGG (SEQ ID NO:3). The first amplification primer selectively hybridizes to A or A' and contains the grafting sequence alpha (e.g., from 5' to 3' AATGA-TACGGCGACCACCGAGATCTACAC (SEQ ID NO:15)). With reference to FIG. 1, this refers to "version 5."

In some embodiments, the tagmentase is a homoadapter-loaded tagmentase that is loaded with the transferred strand comprising the sequence from 5' to 3': AGATGTGTATAAGAGACAG (SEQ ID NO:10), and the second amplification primer comprises from 5' to 3': TCGTCGGCAGCGTCAGATGTGTATAAGAGACAG (SEQ ID NO:18). In this embodiment, an "outer" amplification primer is used to attach a grafting sequence to the end of the cDNA comprising the transferred strand. The "outer" amplification primer can comprise from 5' to 3': CAAGCAGAAGACGGCATACGAGAT[i7]TCGTCGGCAGCGTC (SEQ ID NO:4). The first amplification primer selectively hybridizes to A or A' and contains the grafting sequence alpha (e.g., from 5' to 3' AATGA-TACGGCGACCACCGAGATCTACAC (SEQ ID NO:15)). With reference to FIG. 1, this refers to "version 6."

In some embodiments, the tagmentase is a homoadapter-loaded tagmentase that is loaded with the transferred strand comprising the sequence from 5' to 3': AGATGTGTATAAGAGACAG (SEQ ID NO:10), and the second amplification primer comprises from 5' to 3': GTCTCGTGGGCTCGGAGATGTGTATAAGAGACAG (SEQ ID NO:12). In this embodiment, an "outer" amplification primer is used to attach a grafting sequence to the end of the cDNA comprising the transferred strand. The "outer" amplification primer can comprise from 5' to 3': AATGA-TACGGCGACCACCGAGATCTACAC[i5]GTCTCGTGGGCTCGG (SEQ ID NO:16). The first amplification primer selectively hybridizes to A or A' and contains the grafting sequence alpha (e.g., from 5' to 3' CAAGCAGAAGACGGCATACGAGAT (SEQ ID NO:2)). With reference to FIG. 1, this refers to "version 7."

In some embodiments, the tagmentase is a homoadapter-loaded tagmentase that is loaded with the transferred strand comprising the sequence from 5' to 3': AGATGTGTATAAGAGACAG (SEQ ID NO:10), and the second amplification primer comprises from 5' to 3': TCGTCGGCAGCGTCAGATGTGTATAAGAGACAG (SEQ ID NO:18). In this embodiment, an "outer" amplification primer is used to attach a grafting sequence to the end of the cDNA comprising the transferred strand. The "outer" amplification primer can comprise from 5' to 3': AATGA-TACGGCGACCACCGAGATCTACAC[i5]TCGTCGGCAGCGTC (SEQ ID NO:17). The first amplification primer selectively hybridizes to A or A' and contains the grafting sequence alpha (e.g., from 5' to 3' CAAGCAGAAGACGGCATACGAGAT (SEQ ID NO:2)). With reference to FIG. 1, this refers to "version 8."

Exemplary Heteroadapter Tagmentase Reactions

In some embodiments, the tagmentase is a heteroadapter-loaded tagmentase that is loaded with a first transferred strand comprising the sequence from 5' to 3': GTCTCGTGGGCTCGGAGATGTGTATAAGAGACAG (SEQ ID NO:12), and the second transferred strand comprises from 5' to 3': TCGTCGGCAGCGTCA-GATGTGTATAAGAGACAG (SEQ ID NO:18). In this embodiment, a second amplification primer comprising from 5' to 3': CAAGCAGAAGACGGCATACGAGAT[i7]GTCTCGTGGGCTCGG (SEQ ID NO:3), and a different second amplification primer comprising from 5' to 3' CAAGCAGAAGACGGCATACGAGAT[i7]TCGTCGGCAGCGTC (SEQ ID NO:4) are used to amplify the tagmentase products in combination with the first amplification primer. The first amplification primer selectively hybridizes to A or A' and contains the grafting sequence alpha (e.g., from 5' to 3' AATGATACGGCGAC-CACCGAGATCTACAC (SEQ ID NO:15)). With reference to FIG. 1, this refers to "version 9."

In some embodiments, the tagmentase is a heteroadapter-loaded tagmentase that is loaded with a first transferred strand comprising the sequence from 5' to 3': GTCTCGTGGGCTCGGAGATGTGTATAAGAGACAG (SEQ ID NO:12), and the second transferred strand comprises from 5' to 3': TCGTCGGCAGCGTCA-GATGTGTATAAGAGACAG (SEQ ID NO:18). In this embodiment, a second amplification primer comprising from 5' to 3': AATGATACGGCGACCACCGAGATCTA-CAC[i5]GTCTCGTGGGCTCGG (SEQ ID NO:16), and a different second amplification primer comprising from 5' to 3' AATGATACGGCGACCACCGAGATCTACAC[i5]TCGTCGGCAGCGTC (SEQ ID NO:17) are used to amplify the tagmentase products in combination with the first amplification primer. The first amplification primer selectively hybridizes to A or A' and contains the grafting sequence alpha (e.g., from 5' to 3' AATGATACGGCGAC-CACCGAGATCTACAC (SEQ ID NO:15)). With reference to FIG. 1, this refers to "version 10."

In some embodiments, the tagmentase is a heteroadapter-loaded tagmentase that is loaded with a first transferred strand comprising the sequence from 5' to 3': GTCTCGTGGGCTCGGAGATGTGTATAAGAGACAG (SEQ ID NO:12), and the second transferred strand comprises from 5' to 3': TCGTCGGCAGCGTCA-GATGTGTATAAGAGACAG (SEQ ID NO:18). In this embodiment, a second amplification primer comprising from 5' to 3': AGATGTGTATAAGAGACAG (SEQ ID NO:10) is used to amplify the tagmentase products in combination with the first amplification primer. The first amplification primer selectively hybridizes to A or A' and contains the grafting sequence alpha (e.g., from 5' to 3' AATGATACGGCGACCACCGAGATCTACAC (SEQ ID NO:15)). This amplification product is then amplified with an "outer" amplification primer comprising from 5' to 3': CAAGCAGAAGACGGCATACGAGAT[i7]GTCTCGTGGGCTCGGAGATGTGTATAAGAG ACAG (SEQ ID NO:19) in combination with the first amplification primer. With reference to FIG. 1, this refers to "version 11."

In some embodiments, the tagmentase is a heteroadapter-loaded tagmentase that is loaded with a first transferred strand comprising the sequence from 5' to 3': GTCTCGTGGGCTCGGAGATGTGTATAAGAGACAG (SEQ ID NO:12), and the second transferred strand comprises from 5' to 3': TCGTCGGCAGCGTCA-GATGTGTATAAGAGACAG (SEQ ID NO:18). In this embodiment, a second amplification primer comprising from 5' to 3': AGATGTGTATAAGAGACAG (SEQ ID NO:10) is used to amplify the tagmentase products in combination with the first amplification primer. The first amplification primer selectively hybridizes to A or A' and contains the grafting sequence alpha (e.g., from 5' to 3' AATGATACGGCGACCACCGAGATCTACAC (SEQ ID NO:15)). This amplification product is then amplified with a first "outer" amplification primer comprising from 5' to 3': GTCTCGTGGGCTCGGAGATGTGTATAAGAGACAG (SEQ ID NO:12) and a second "outer" amplification primer comprising from 5' to 3': CAAGCAGAAGACGGCAT-ACGAGAT[i7]GTCTCGTGGGCTCGG (SEQ ID NO:3) in combination with the first amplification primer. With reference to FIG. 1, this refers to "version 12."

In some embodiments, the tagmentase is a heteroadapter-loaded tagmentase that is loaded with a first transferred strand comprising the sequence from 5' to 3': GTCTCGTGGGCTCGGAGATGTGTATAAGAGACAG (SEQ ID NO:12), and the second transferred strand comprises from 5' to 3': TCGTCGGCAGCGTCAGATGTGTATAAGAGACAG (SEQ ID NO:18). In this embodiment, a second amplification primer comprising from 5' to 3': AGATGTGTATAAGAGACAG (SEQ ID NO:10) is used to amplify the tagmentase products in combination with the first amplification primer. The first amplification primer selectively hybridizes to A or A' and contains the grafting sequence alpha (e.g., from 5' to 3' CAAGCAGAAGACGGCATACGAGAT (SEQ ID NO:2)). This amplification product is then amplified with an "outer" amplification primer comprising from 5' to 3': AATGATACGGCGACCACCGAGATCTACAC[i5]TCGTCGGCAGCGTCAGATGTGTATA AGAGACAG (SEQ ID NO:20) in combination with the first amplification primer. With reference to FIG. 1, this refers to "version 13."

In some embodiments, the tagmentase is a heteroadapter-loaded tagmentase that is loaded with a first transferred strand comprising the sequence from 5' to 3': GTCTCGTGGGCTCGGAGATGTGTATAAGAGACAG (SEQ ID NO:12), and the second transferred strand comprises from 5' to 3': TCGTCGGCAGCGTCAGATGTGTATAAGAGACAG (SEQ ID NO:18). In this embodiment, a second amplification primer comprising from 5' to 3': AGATGTGTATAAGAGACAG (SEQ ID NO:10) is used to amplify the tagmentase products in combination with the first amplification primer. The first amplification primer selectively hybridizes to A or A' and contains the grafting sequence alpha (e.g., from 5' to 3' CAAGCAGAAGACGGCATACGAGAT (SEQ ID NO:2)). This amplification product is then amplified with a first "outer" amplification primer comprising from 5' to 3': TCGTCGGCAGCGTCAGATGTGTATAAGAGACAG (SEQ ID NO:18) and a second "outer" amplification primer comprising from 5' to 3': AATGATACGGCGACCACCGAGATCTACAC[i5]TCGTCGGCAGCGTC (SEQ ID NO:17) in combination with the first amplification primer. With reference to FIG. 1, this refers to "version 14."

In some embodiments, after tagmentation to transfer the transferred strand of the tagmentase to the 5' end of the second strand cDNA molecule, the product is amplified with a hot-start method. For example, the amplification can be performed with a hot-start DNA polymerase. Alternatively, polymerase or another essential reagent, such as the polymerase and/or nucleotide triphosphates can be added after the reaction has reached a temperature that is too high to permit substantial polymerase-mediated extension. Alternatively, reagents for amplification can be assembled at a temperature that is too low to permit substantial polymerase-mediated extension (e.g., 4° C., <25° C. or about 25° C.) and then immediately transferred to an incubator to ramp the temperature above the permissive temperature before substantial extension can occur. For example, reagents can be assembled on ice and then transferred to a thermalcycler set at a denaturation temperature. PCR amplification can then be initiated by 2 or 3-step thermal cycling.

III. Kits

Described herein are kits that contain one or more primers, such as a mixture of two different second amplification primers described herein, or a mixture of two different sequencing primers described herein.

EXAMPLES

Example 1: Second Strand Direct

A library of barcoded hydrogel particles is mixed with a sample of cells in a microfluidic device and co-encapsulated into aqueous droplets containing reagents to lyse the cells and perform reverse transcription of the RNA of the cells. The encapsulation is performed under conditions such that at least 95% of the droplets contain no more than one cell. Upon co-encapsulation, the lysis reagent lyses the cell. The oligos are released from the hydrogel particles by cleaving the oligos at their 5' end. Uracil bases positioned at the 5' most position of the hydrogel particle oligo are excised using Uracil DNA glycosylase (UDG) and the DNA glycosylase-lyase Endonuclease VIII. The oligo cleaving reaction is performed so that cell lysis and downstream reverse transcription are not inhibited. The temperature is increased to 50° C. to support first strand synthesis by the reverse transcription enzyme present in the droplets. The reverse transcription enzyme does not possess RNASEH activity. First strand synthesis appends a cellular barcode to every transcript that is reverse transcribed in the droplet. The emulsion is broken. The first strand synthesis products are pooled into a single reaction mixture. Since the RNA is already barcoded, the remaining sequencing steps can be performed without maintaining physical partitioning.

Upon breaking the emulsion, the unincorporated oligonucleotides are removed by EXOI treatment and Ampure bead size selection. The cDNA:RNA hybrids are then converted to double stranded cDNA by performing second strand synthesis using a combination of enzymes. RNASEH is introduced into the reaction mixture to nick the RNA molecules. DNA polymerase I synthesizes the second strand by performing DNA template directed DNA synthesis after initiating DNA synthesis from an RNA primer. The DNA polymerase possesses a 5 to 3' exonuclease activity to maintain processivity through RNA: DNA hybrids or DNA: DNA hybrids that occur on the template molecule. DNA ligases are included during second synthesis to create intact second strand cDNA molecules. The oligonucleotide sequence from the barcoded particles is synthesized as part of second strand synthesis resulting in the incorporation of the oligonucleotide sequence in the second strand. Second strand synthesis is performed at 16° C. Upon completion of second strand synthesis, the double stranded cDNA is purified using Ampure beads.

Nextera tagmentation is then performed on the double stranded DNA. A single heteroadapter loaded Tn5 transposase is used whereby each of the two adapters in a single Tn5 particle contains a different single stranded adapter region. After tagmentation, the newly synthesized second strand has both the hydrogel particle oligonucleotide sequence (TSO-AC) and a transferred nextera adapter sequence (Tag adapter). Thus, prior to post tagmentation PCR, gap filling is not required and the 72° C. gap fill step is omitted from the thermal protocol. The reaction components are maintained on ice or at room temperature and placed directly on a thermocyler preheated to 95° C. The PCR primers target the hydrogel particle oligo and one the two nextera adapter sequence. The Illumina flow cell grafting sequences P5 and P7 are appended to opposite ends of the amplified fragments during PCR. The number of PCR cycles is limited to 13 to provide sufficient material for NGS.

Example 2: Results from a Second Strand Direct Experiment

Figure 4:
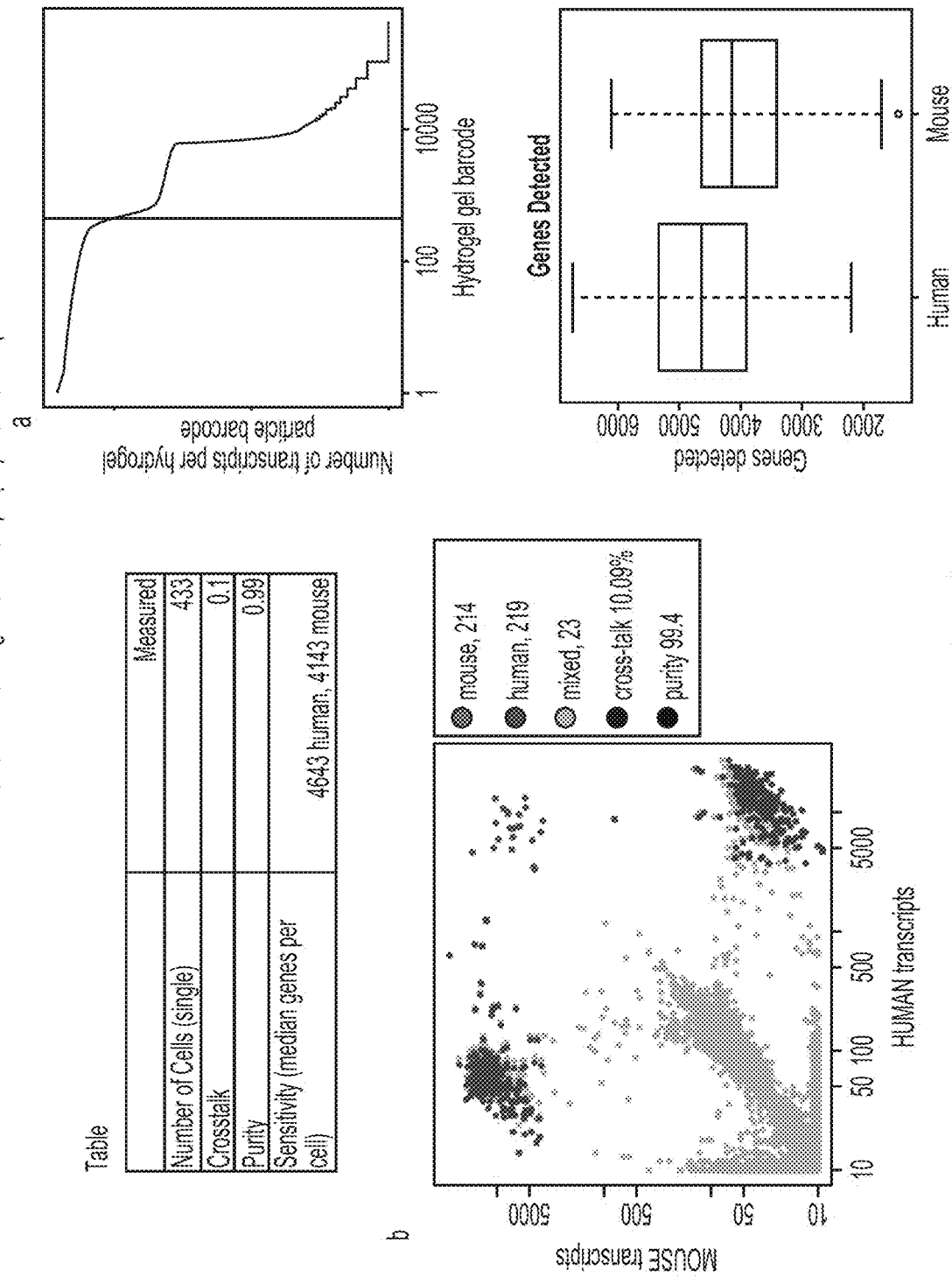
FIG. 4 illustrates results from a second strand direct protocol performed as described in Example 2.

The second strand direct protocol was performed as described in example 1, whereby a 50:50 mixture of mouse and human cells was used. After NGS sequencing using an Illumina sequencer, the data were grouped together and rank ordered according to the number of transcripts per hydrogel particle barcode sequence (FIG. 4a). The top 433 data points were considered single cell data points (data left of the vertical line in FIG. 4a). FIG. 4b plots the cell barcode data points according to their mouse and (vertical axis) and human (horizontal axis) content. The cell barcodes with the greatest number of transcripts are considered single cells (identified by what is left of vertical line in FIG. 4a). Some data points have both human and mouse transcripts and these define the crosstalk statistic, here calculated as 0.1. Purity refers to how pure the single cell data is compared to the supernatant RNA levels (data points right of the vertical line shown in FIG. 4a), and here it was calculated as 0.99. Lastly, the number of genes per cell was analyzed using the transcript information. Here a median of 4643 human or 4143 mouse genes per single cell were calculated.

Example 3: Results from Multiple Second Strand Direct Experiments Showing Reproducibility The second strand direct protocol was performed multiple times as described in example 1, whereby by a 50:50 mixture of mouse and human cells were used. The data was analyzed as described in example 2. FIG. 5 shows the reproducibility of the method for 4 independent experiments across 3 different users and 2 different hydrogel particle lots.

Example 4: Improving Sensitivity by Using a Homoadapter Tagmentase

Figure 6A:
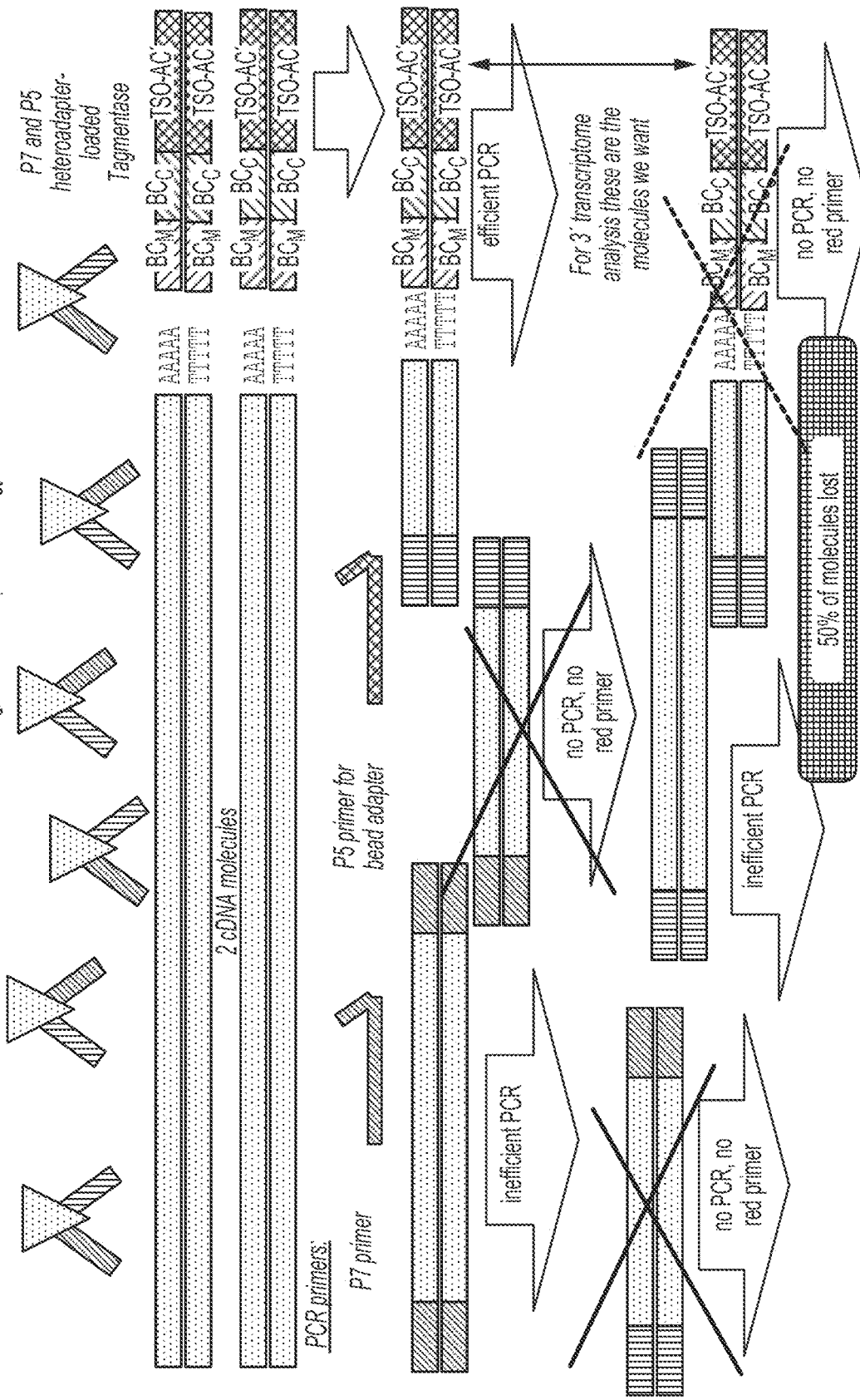
FIG. 6a illustrates a mechanism by which 50% of the desired adapter tagged molecules fail to be efficiently amplified in a post-tagmentation step of PCR amplification. Typically the post-tagmentation step of PCR amplification is used to append flow cell grafting sequences to the ends of the target molecules. Thus, 50% this mechanism can result in a lack of sequencing data for 50% of the desired adapter tagged molecules.
Figure 6B:
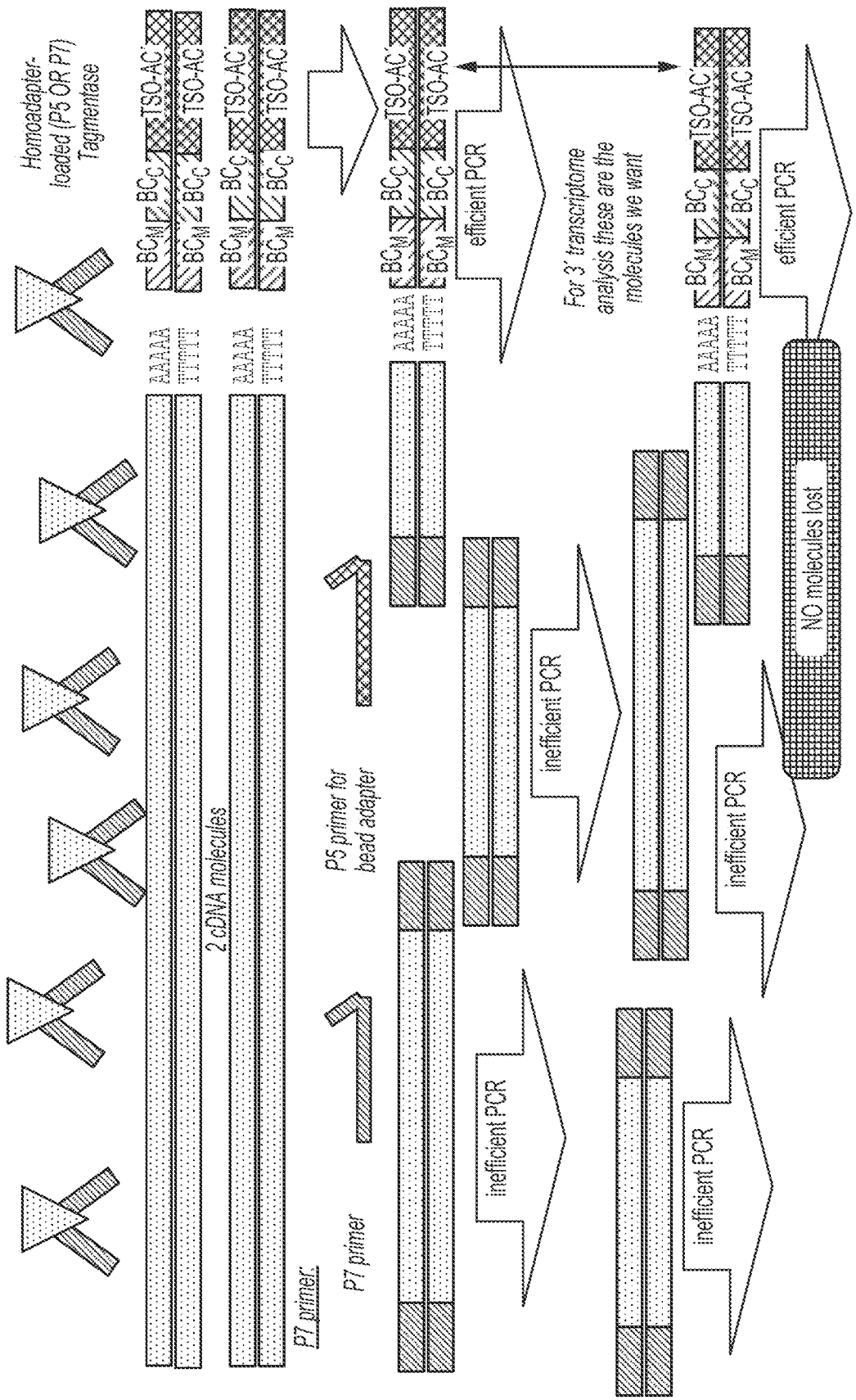

Using commercially available Nextera tagmentase loaded with heteroadapters, the adapter is inserted into the double stranded cDNA immediately adjacent to the hydrogel particle oligo adapter half the time (FIG. 6a). These molecules do not form clusters on an Illumina flow cell and are lost from analysis since they are not amplified and tagged with P5 and P7 during post tagmentation PCR. Since the double stranded cDNA is not amplified pre tagmentation this leads to a 50% loss in sensitivity. Using a homoadapter loaded Nextera tagmentase, however, results in the insertion of amplifiable double stranded cDNA molecules immediately adjacent to the hydrogel particle oligo adapter for 100% of tagmentation events (FIG. 6b). Thus, all molecules with a hydrogel particle oligo adapter on one end that are tagmented with a homoadatper tagmentase are PCR amplified and tagged with P5 and P7 at opposite ends. The double-tagged molecules are all able to form clusters on a flow cell and are all potentially analyzable leading to optimal sensitivity of input cDNA molecules. The gap fill post tagmentation at 72° C. is shown for FIGS. 6a-6b. With this polymerization step, enrichment can involve PCR suppression due to end fragment homology.

Figure 7A:
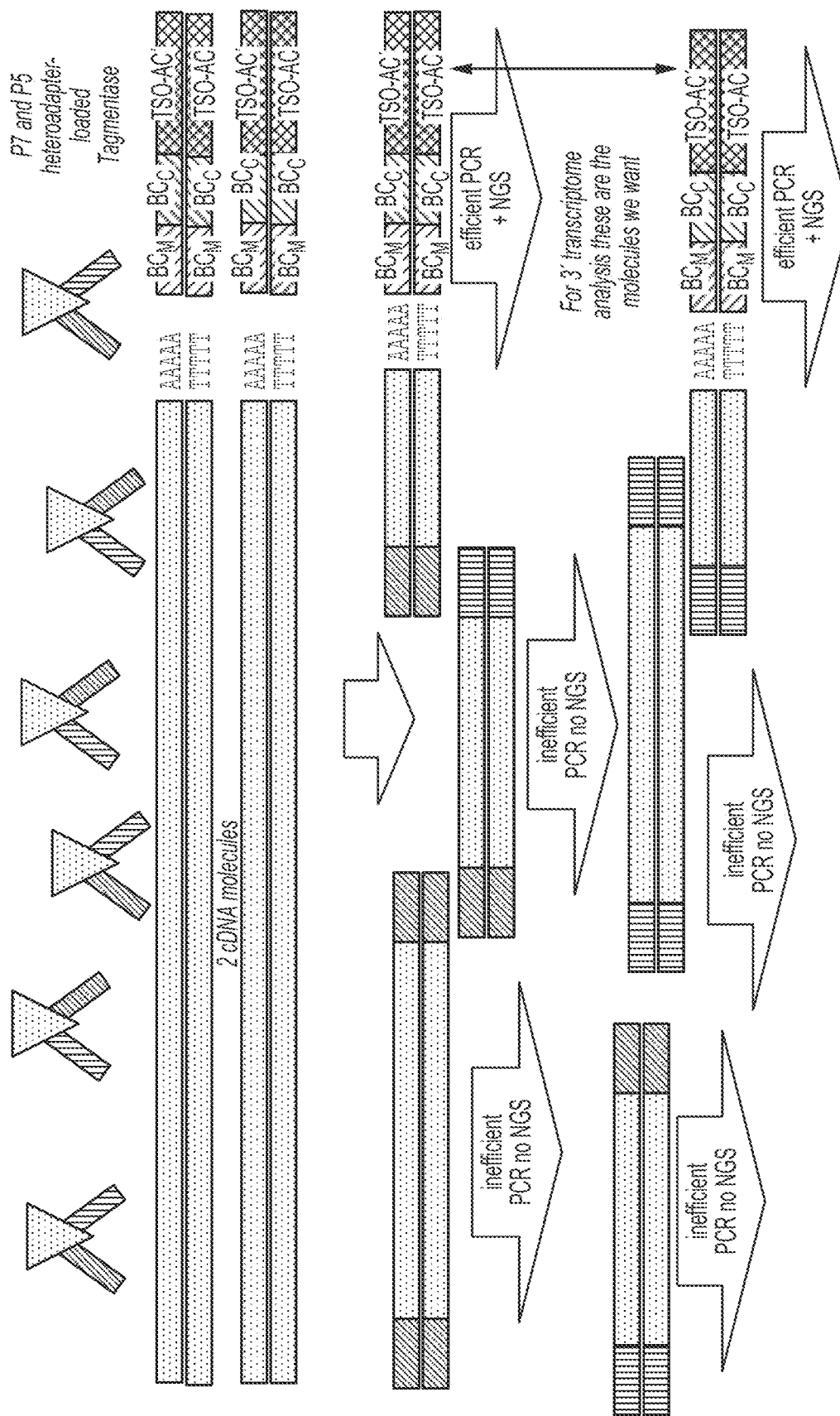
Figure 7B:
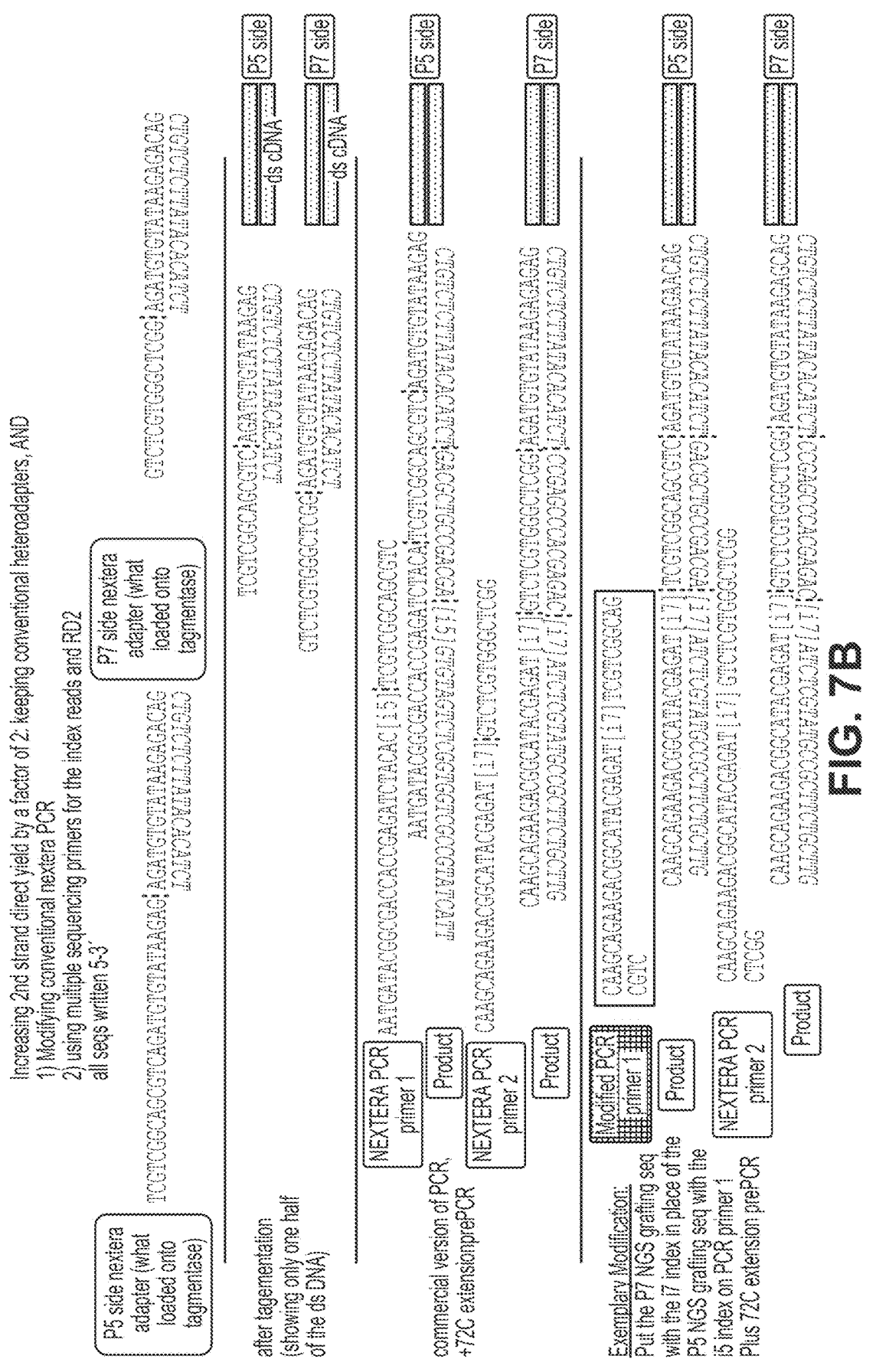
Figure 7C:
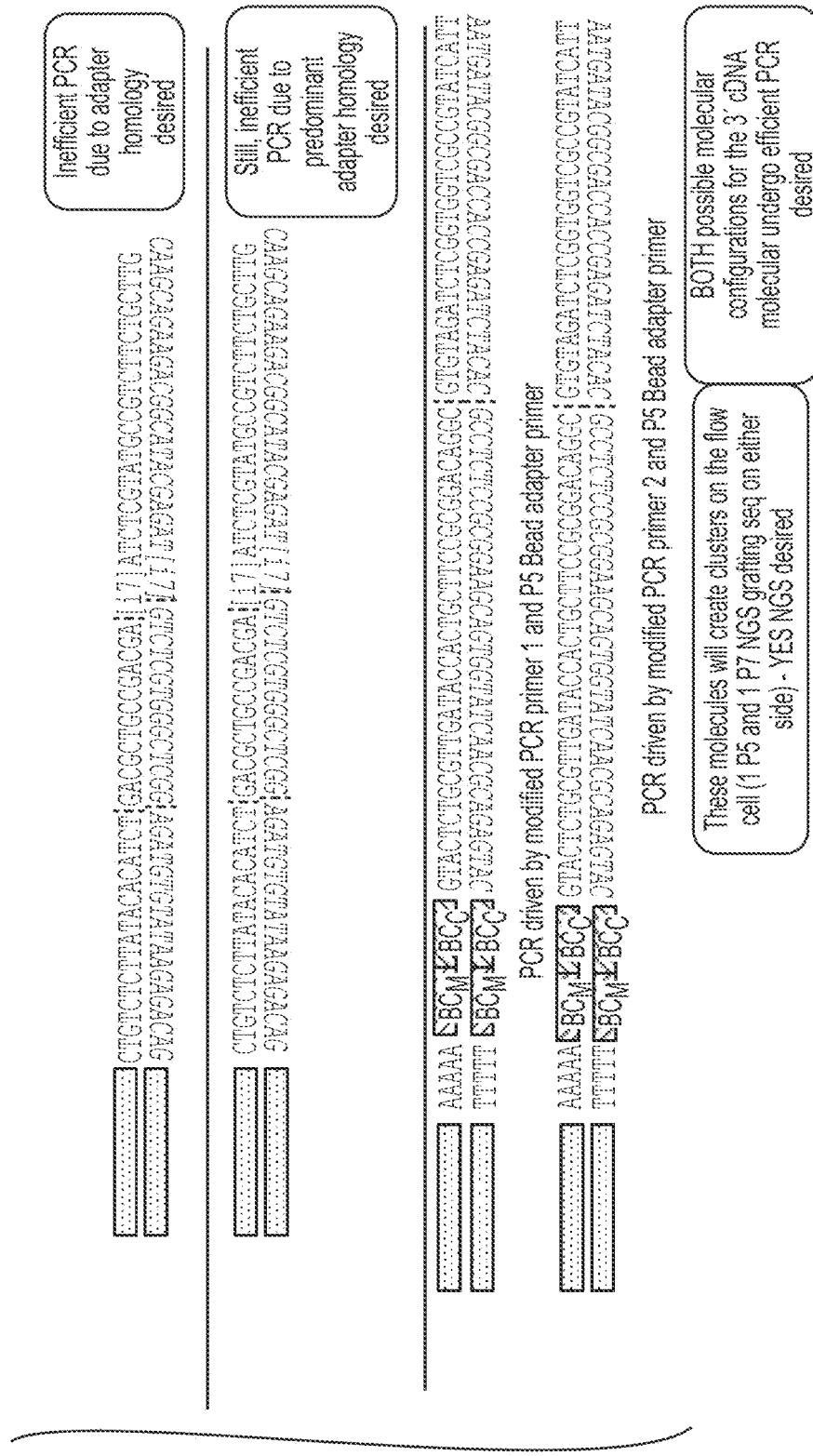
Figure 7D:
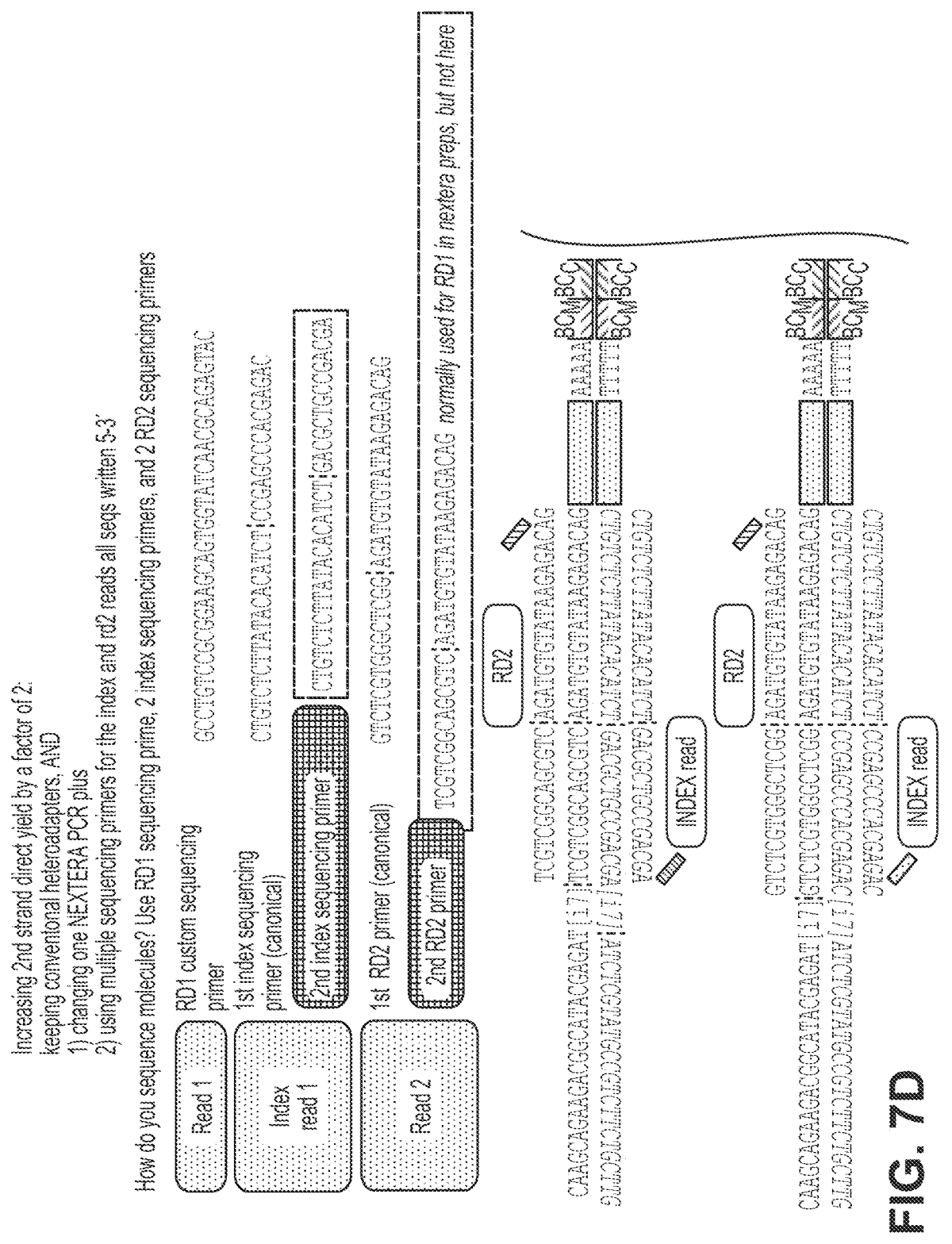
Figure 7D:
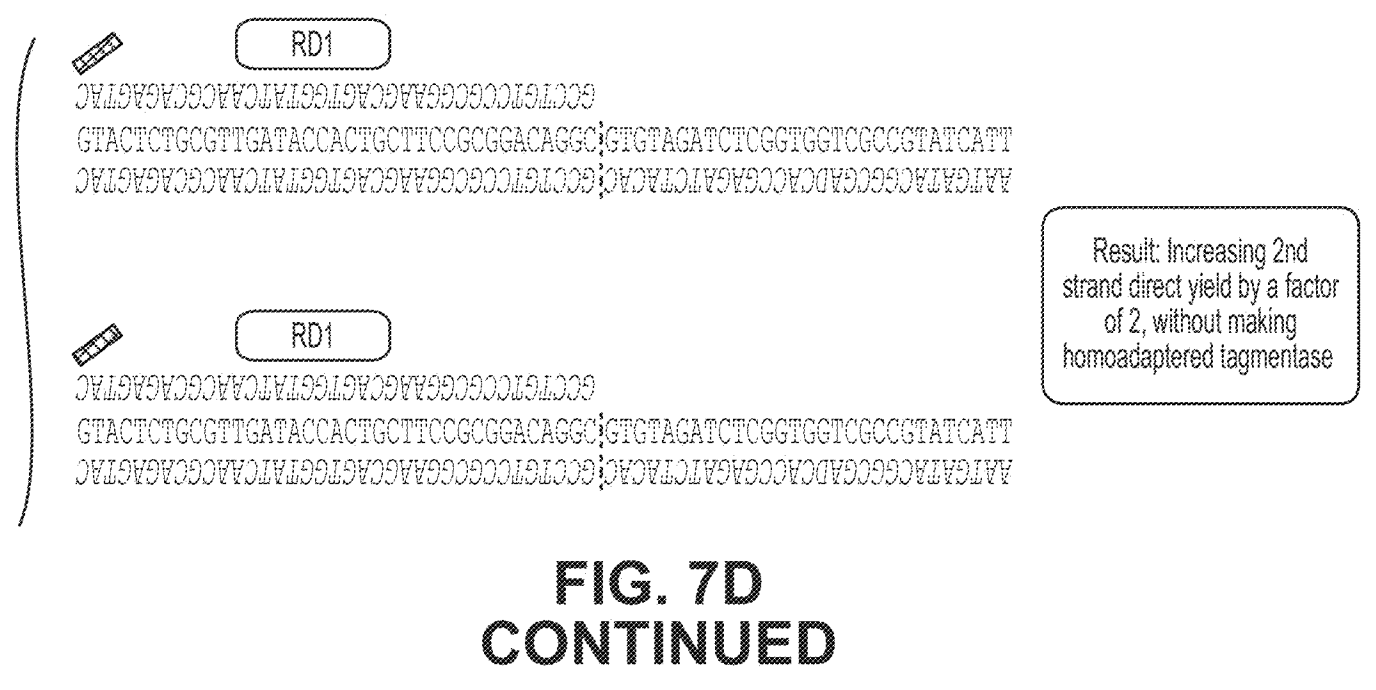

Example 5: Improving Sensitivity Using a Heteroadapter Tagmentase and Using 3 Primer Post Tagmentation PCR and Multiple Sequencing Primers During NGS Using commercially available Nextera tagmentase loaded with heteroadapters, and the commercially available primer that amplifies one Nextera adapter, half of the molecules that have the other Nextera adapter are lost from analysis (refer to Example 4 for additional information). Amplifying both Nextera adapters would optimize sensitivity (FIG. 7a) and this is possible by performing 3 primer PCR post tagmentation as shown in FIG. 7b. A novel primer is used, whereby the P7 grafting sequence is appended to a sequence that normally binds the Nextera adapter that is usually tagged with the P5 grafting sequence. Thus, both Nextera adapters are tagged with P7 and provided the hydrogel particle oligo adapter is tagged with P5 all tagmented fragments are amplified. In this example, a 72° C. gap fill is included, and FIG. 7c illustrates the various molecule constructs produced by tagmentation, gap fill and PCR using the 3 primer system. The non-hydrogel particle adapted molecules still are subjected to PCR suppression due to extensive end fragment homology. Conversely the hydrogel particle adaptered molecules undergo efficient PCR due to a lack of end fragment homology as shown. FIG. 7d illustrates how to sequence the adaptered molecules produced from a heteroadapter tagmentase and 3 primer PCR (FIG. 7b). As shown, a mixture of 2 index sequencing primers are used during post tagmentation PCR. During paired end sequencing, a mixture of 2 Read 2 sequencing primers are used to target both Nextera adapters and to enable sequencing of both Nextera tagmented fragments.

Figure 8A:
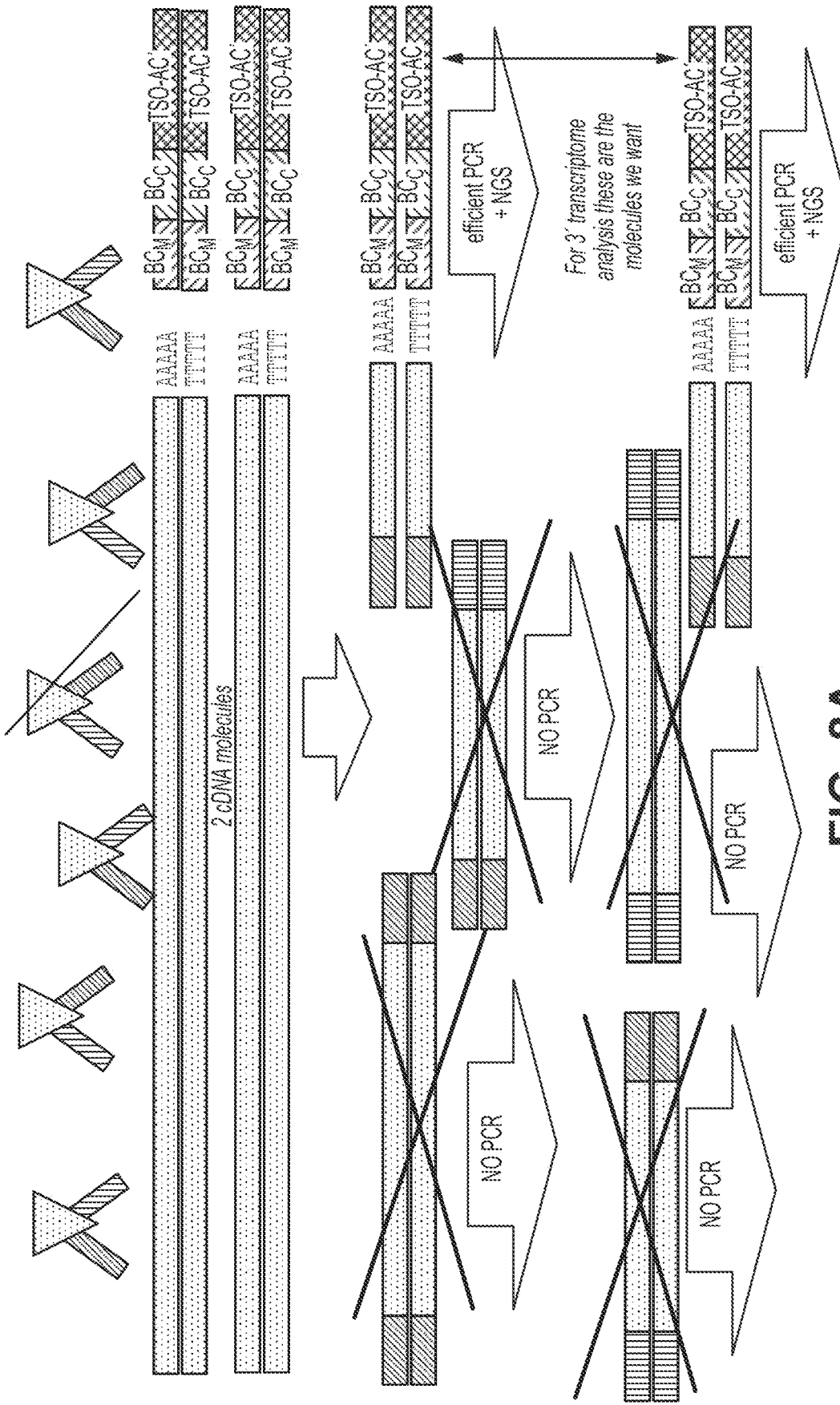
Figure 8B:
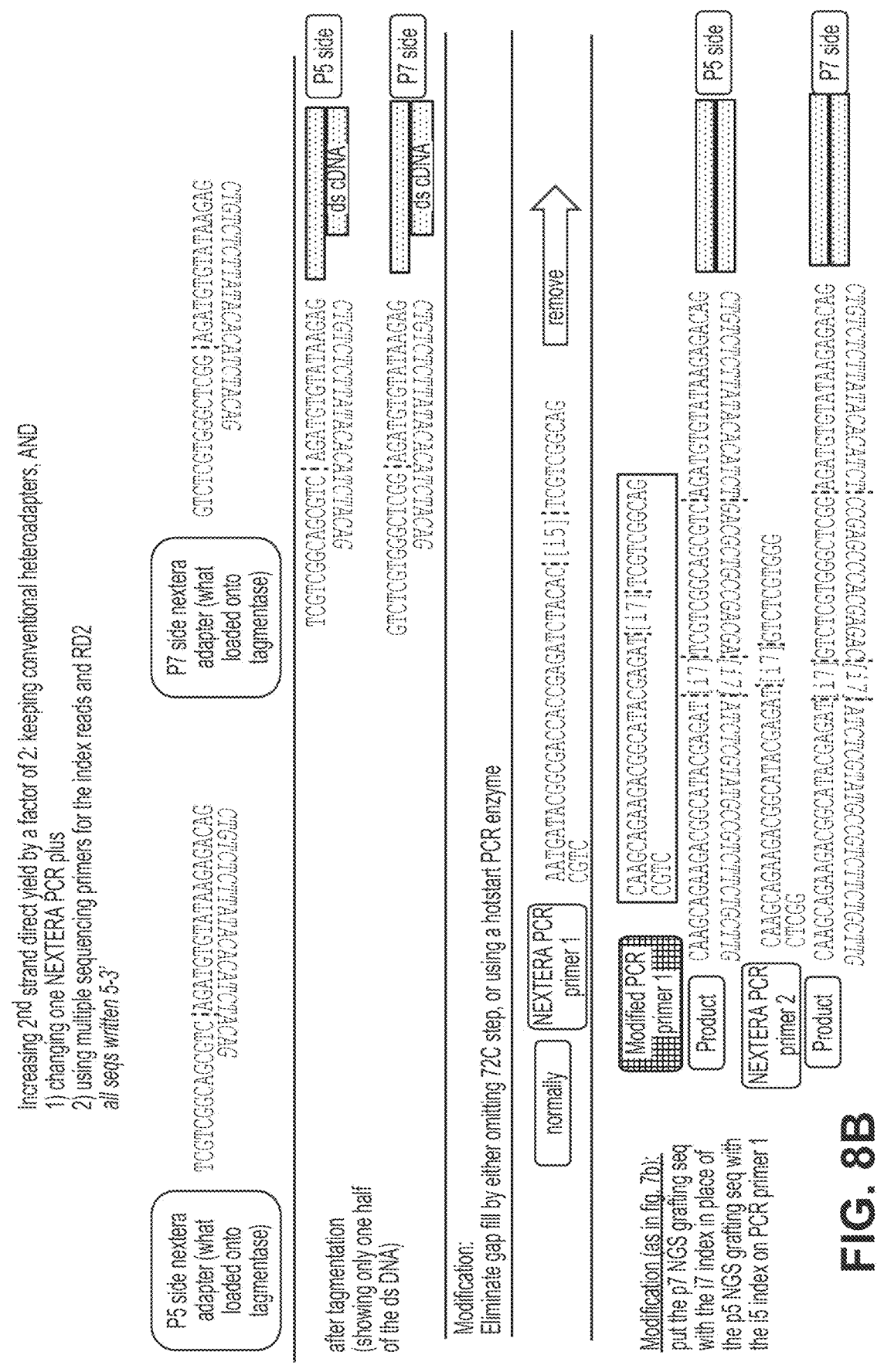
Figure 8D:
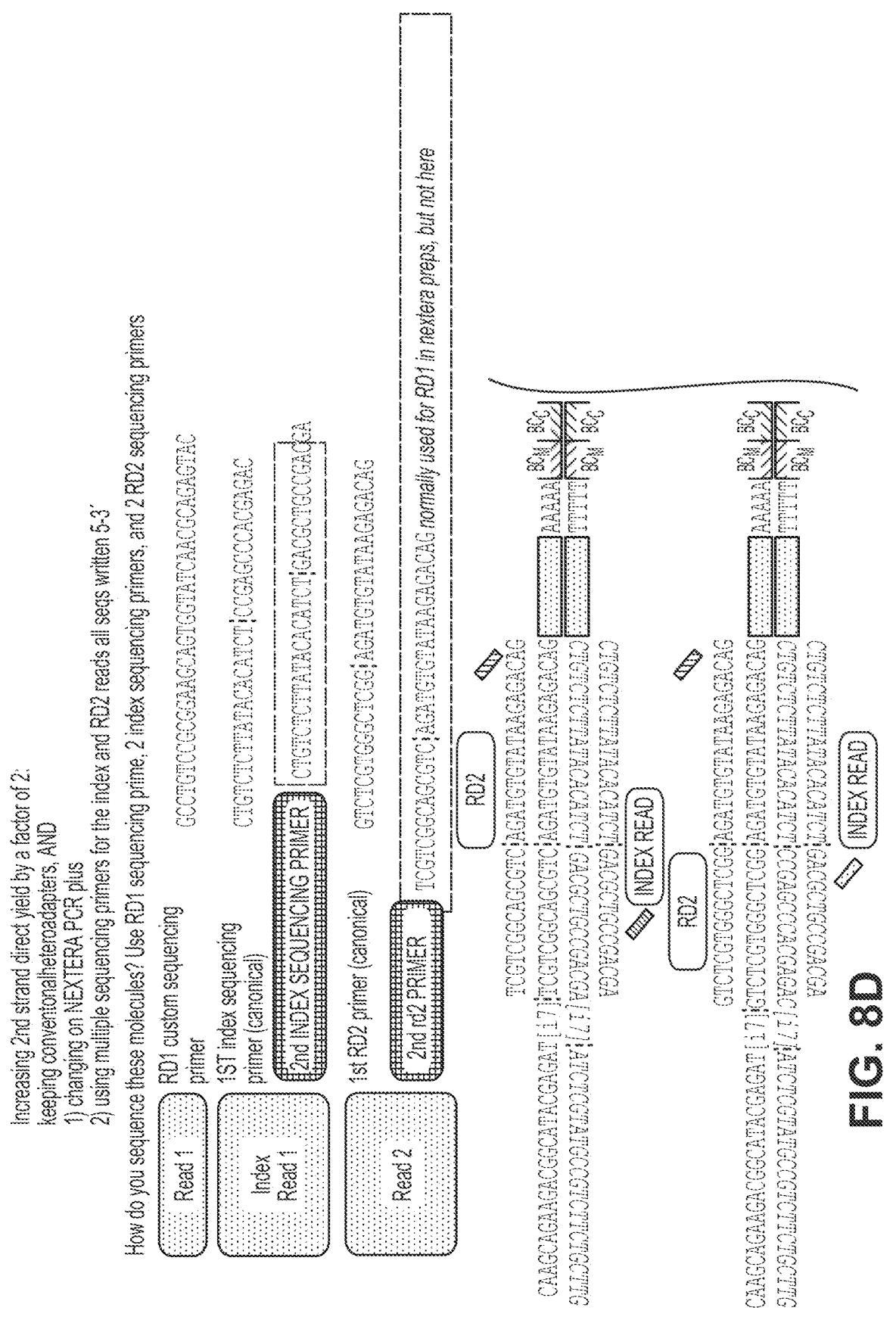

Example 6: Improving Sensitivity Using a Heteroadapter Tagmentase and Using 3 Primer Post Tagmentation PCR and Multiple Sequencing Primers During NGS and Omitting the Gap Fill Post Tagmentation To improve specificity during Nextera PCR, it is desirable to eliminate any possible PCR of non hydrogel particle oligo adaptered fragments (FIG. 8a). This can be performed by omitting the prePCR gap fill from the procedure (FIG. 8b). This results in molecules that do not have primer binding sites during the first cycle of PCR (FIG. 8c). Hydrogel particle oligo adaptered fragments, however, have a PCR primer binding site. During the first few cycles of PCR, when these molecules are copied, they provide de novo Nextera adapter PCR primer sites on the non hydrogel particle oligo adaptered end of the tagmented fragments. The result is that the two ends of hydrogel particle oligo adaptered fragments are all PCR amplifiable. Since 3 primer PCR is performed (FIG. 8b), tagmented fragmented with either heteroadapter are amplified. These molecules are sequenced with novel primer mixtures as described in Example 5 (FIG. 8d).

Example 7: Performance of Amplifying and Sequencing Both Nextera Adapters

Figure 9A:
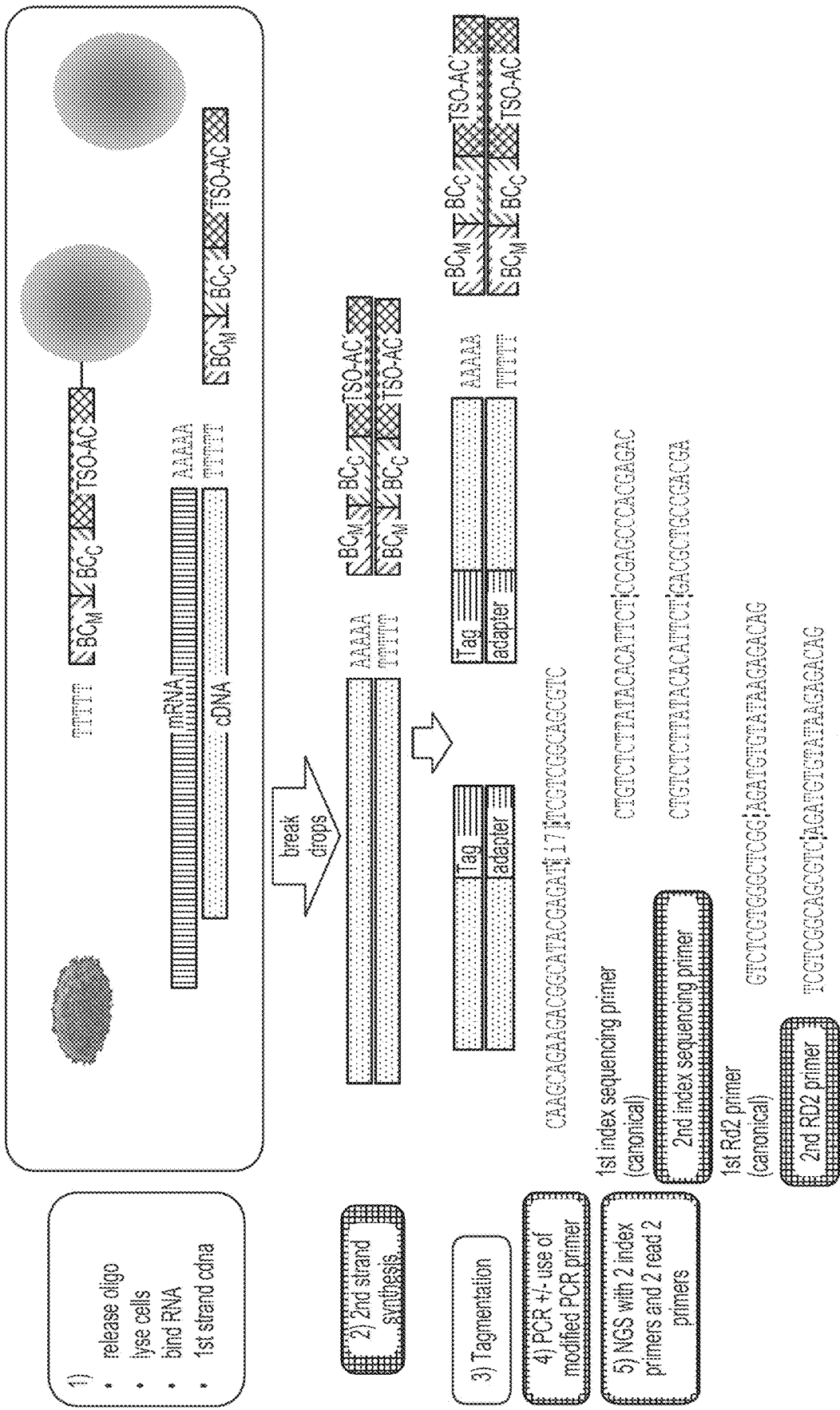
FIGS. 9a-9b illustrate a workflow (FIG. 9a) and high-throughput sequencing results (FIG. 9b) in a library prepared with heteroadapter loaded tagmentases to produce products that were then amplified with a mixture of two different second primers in combination with a first primer.
Figure 9B:
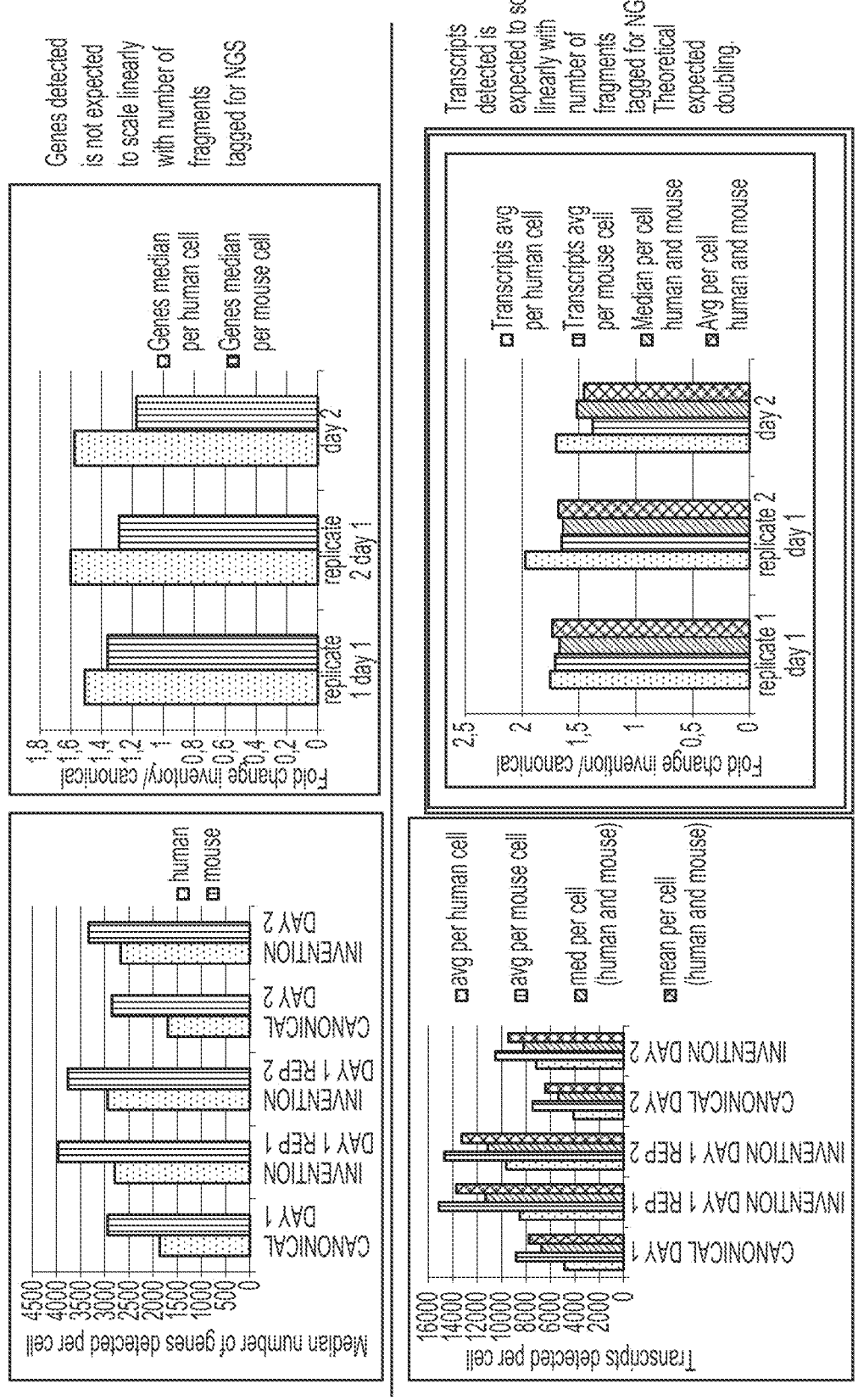

The second strand direct protocol as described in Example 6 is illustrated in FIG. 9a. The modified PCR primer used in 3 primer PCR is shown as well as the required mixtures of sequencing primers for the index read and read 2. Improved sensitivity for both genes and transcripts detected per cell is shown (FIG. 9b) with a 1.4 to 2 fold improvement in sensitivity when detecting both Nextera adapters and all tagmented fragments. Results from experiments performed on multiple days and technical replicates are shown.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for tagging a cDNA polynucleotide, the method comprising:
providing a double-stranded mRNA: cDNA hybrid comprising a first strand cDNA polynucleotide having a 5' end and a 3' end and hybridized to a complementary mRNA having a 5' end and a 3' end, wherein the 5' end of the first strand cDNA polynucleotide comprises a first adapter sequence or complement thereof;
synthesizing one or more second strand cDNA polynucleotides that are complementary to and hybridized to the first strand cDNA polynucleotide, wherein the synthesizing comprises:
i) hybridizing random primers to the first strand cDNA of the mRNA: cDNA hybrid and extending hybridized random primers to form the one or more second strand cDNA polynucleotides;
contacting the double-stranded cDNA polynucleotide with an adapter-loaded tagmentase, thereby forming a reaction mixture comprising a tagged double-stranded cDNA polynucleotide comprising a first end and a second end, wherein the first end comprises the first adapter sequence and complement thereof, and the second end comprises a second adapter sequence and complement thereof,
forming partitions comprising (a) amplification primers comprising at least one primer comprising a partition-specific barcode and (b) the first strand cDNA and the second strand cDNAs and
amplifying the first and second strand cDNAs with the amplification primers.

2. The method of claim 1, wherein the 5' end of the mRNA is single-stranded.

3. The method of claim 1, wherein the amplification primers comprise (i) a first amplification primer that selectively hybridizes to the first adapter sequence and comprises a first sequencing-platform-specific adapter sequence, and wherein (ii) a second amplification primer that selectively hybridizes to the second adapter sequence and comprises a second sequencing-platform-specific adapter sequence, thereby producing a sequencing platform-specific cDNA amplicon.

4. The method of claim 1, wherein the providing the double-stranded mRNA: cDNA hybrid comprises contacting the mRNA with a reverse transcriptase and a first strand synthesis primer to thereby extend the first strand synthesis primer in an mRNA template-directed DNA polymerase reaction, wherein the first strand synthesis primer comprises a 3' poly-thymine end region and a 5' end comprising the first adapter sequence or complement thereof, thereby synthesizing the first strand cDNA polynucleotide hybridized to the complementary mRNA, and wherein the 5' end of the first strand cDNA comprises the first adapter sequence or complement thereof.

5. The method of claim 4, wherein the method comprises performing the mRNA template-directed DNA polymerase reaction in a reaction mixture comprising mRNA, and the contacting the mRNA: cDNA hybrid with the enzyme comprising RNase H activity is performed in a reaction mixture comprising mRNA from at least 10 cells.

6. The method of claim 4, wherein the method comprises performing the mRNA template-directed DNA polymerase reaction in a reaction mixture comprising mRNA from at least 10 cells.

7. The method of claim 4, wherein the first strand synthesis primer comprises a molecular barcode.

8. The method of claim 1, wherein the 5' end of the first strand cDNA polynucleotide comprises a molecular barcode.

9. The method of claim 3, wherein: the first end of the tagged double-stranded cDNA polynucleotide comprises adapter sequence A and the second end of the tagged double-stranded cDNA polynucleotide comprises adapter sequence B, and the method comprises selectively amplifying from the reaction mixture the tagged double-stranded cDNA polynucleotide, thereby producing a sequencing platform-specific cDNA amplicon, by contacting the tagged double-stranded cDNA polynucleotide with the first amplification primer, the second amplification primer, and a third amplification primer,
wherein the first amplification primer comprises a 3' region having a sequence A' that selectively hybridizes to the first adapter sequence A and the first amplification primer further comprises a 5' region comprising a first sequencing-platform-specific adapter sequence; and wherein the second amplification primer and third amplification primer each comprise a 5' region comprising a second sequencing-platform-specific adapter sequence, and a 3' region, wherein the 3' region of the second or third amplification primer has a sequence B' that selectively hybridizes to the second adapter sequence B.

10. The method of claim 1, wherein the contacting the double-stranded cDNA polynucleotide with the adapter-loaded tagmentase comprises introducing a homoadapter-loaded tagmentase comprising two identical polynucleotide adapters into the reaction mixture comprising the double-stranded cDNA polynucleotide, thereby attaching one of the polynucleotide adapters to the second end of the double-stranded cDNA.

11. The method of claim 10, wherein the attaching is performed in a reaction mixture that does not comprise an adapter-loaded tagmentase comprising a polynucleotide adapter that is different from the two identical polynucleotide adapters of the homoadapter-loaded tagmentase.

12. The method of claim 1, wherein the contacting the double-stranded cDNA polynucleotide with the adapter-loaded tagmentase comprises:

introducing a heteroadapter-loaded tagmentase comprising two structurally distinct polynucleotide adapters into the reaction mixture comprising the double-stranded cDNA polynucleotide; or introducing into the reaction mixture comprising the double-stranded cDNA polynucleotide a first and a second homoadapter-loaded tagmentase wherein the first homoadapter-loaded tagmentase comprises a polynucleotide adapter and the second homoadapter tagmentase comprises a structurally distinct polynucleotide adapter, thereby attaching one of the polynucleotide adapters to the second end of the double-stranded cDNA.

13. The method of claim 1, wherein the double-stranded cDNA polynucleotide contacted with the adapter-loaded tagmentase comprises an original first strand cDNA polynucleotide hybridized to an original second strand cDNA polynucleotide.

14. The method of claim 1, wherein the partitions are droplets in an emulsion.

15. The method of claim 1, wherein the partitions are microwells, nanowells, or picowells.

16. A method for tagging a plurality of cDNA polynucleotides, the method comprising performing a method according to claim 1 with a plurality of structurally distinct mRNA:cDNA hybrids.

17. The method of claim 16, wherein the plurality of structurally distinct mRNA:cDNA hybrids comprise mRNA from a single cell.

18. The method of claim 16, wherein the plurality of structurally distinct mRNA:cDNA hybrids comprise mRNA from at least 10 cells.

* * * * *